(12) United States Patent
Itkowitz et al.

(10) Patent No.: US 10,660,716 B2
(45) Date of Patent: *May 26, 2020

(54) SYSTEMS AND METHODS FOR RENDERING ONSCREEN IDENTIFICATION OF INSTRUMENTS IN A TELEOPERATIONAL MEDICAL SYSTEM

(71) Applicant: INTUITIVE SURGICAL OPERATIONS, INC., Sunnyvale, CA (US)

(72) Inventors: Brandon D. Itkowitz, San Jose, CA (US); Paul W. Mohr, Mountain View, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/558,918

(22) Filed: Sep. 3, 2019

(65) Prior Publication Data

US 2019/0388168 A1    Dec. 26, 2019

Related U.S. Application Data

(63) Continuation of application No. 15/558,466, filed as application No. PCT/US2016/022573 on Mar. 16, 2016, now Pat. No. 10,433,922.

(Continued)

(51) Int. Cl.
*A61B 34/00* (2016.01)
*A61B 34/35* (2016.01)
(Continued)

(52) U.S. Cl.
CPC .............. *A61B 34/35* (2016.02); *A61B 34/25* (2016.02); *A61B 34/37* (2016.02); *A61B 34/74* (2016.02);
(Continued)

(58) Field of Classification Search
None
See application file for complete search history.

(56) References Cited

U.S. PATENT DOCUMENTS

| 5,689,717 A | 11/1997 | Pritt et al. |
| 10,433,922 B2 | 10/2019 | Itkowitz et al. |

(Continued)

FOREIGN PATENT DOCUMENTS

| CN | 102341046 A | 2/2012 |
| JP | 2001104333 A | 4/2001 |

(Continued)

OTHER PUBLICATIONS

Extended European Search Report for Application No. EP16765624.8, dated Sep. 17, 2018, 8 pages.

(Continued)

*Primary Examiner* — David H Chu
(74) *Attorney, Agent, or Firm* — Haynes and Boone, LLP

(57) ABSTRACT

A system comprises an operator control system and a plurality of manipulators configured for teleoperation by the operator control system. A first manipulator controls movement of a first medical instrument. A second manipulator controls movement of a second medical. A third manipulator controls movement of an imaging instrument. The system also comprises a processing unit configured to determine an initial position for a first badge associated with a distal end portion of the first medical instrument, determine an initial position for a second badge associated with a distal end portion of the second medical instrument, evaluate a display factor based on the initial positions of the first and second badges, determine a display position for the first badge in an image coordinate space based on the display factor; and, determine a display position for the second badge in the image coordinate space based on the display factor.

20 Claims, 18 Drawing Sheets

Related U.S. Application Data

(60) Provisional application No. 62/134,294, filed on Mar. 17, 2015.

(51) Int. Cl.

| | | |
|---|---|---|
| *A61B 34/37* | (2016.01) | |
| *A61B 90/94* | (2016.01) | |
| *A61B 90/00* | (2016.01) | |
| *A61B 34/10* | (2016.01) | |
| *B25J 9/16* | (2006.01) | |

(52) U.S. Cl.
CPC .............. *A61B 90/36* (2016.02); *A61B 90/37* (2016.02); *A61B 90/94* (2016.02); *A61B 2034/102* (2016.02); *A61B 2034/107* (2016.02); *A61B 2090/0807* (2016.02); *A61B 2090/373* (2016.02); *B25J 9/1664* (2013.01)

(56) References Cited

U.S. PATENT DOCUMENTS

| | | |
|---|---|---|
| 2004/0046711 A1 | 3/2004 | Triebfuerst |
| 2006/0258938 A1 | 11/2006 | Hoffman et al. |
| 2007/0271500 A1 | 11/2007 | Theophil et al. |
| 2008/0004603 A1 | 1/2008 | Larkin et al. |
| 2010/0201684 A1 | 8/2010 | Yadav et al. |
| 2011/0306986 A1 | 12/2011 | Lee et al. |
| 2014/0055489 A1 | 2/2014 | Itkowitz et al. |
| 2014/0139545 A1 | 5/2014 | Tanikawa et al. |
| 2014/0276944 A1 | 9/2014 | Farritor et al. |
| 2017/0165013 A1 | 6/2017 | Itkowitz et al. |
| 2018/0092700 A1 | 4/2018 | Itkowitz et al. |

FOREIGN PATENT DOCUMENTS

| | | |
|---|---|---|
| JP | 2002253574 A | 9/2002 |
| JP | 2002542362 A | 12/2002 |
| WO | WO-2008002830 A2 | 1/2008 |
| WO | WO-2012158458 A2 | 11/2012 |
| WO | WO-2014104088 A1 | 7/2014 |
| WO | WO-2014160086 A2 | 10/2014 |

OTHER PUBLICATIONS

International Preliminary Report on Patentability for Application No. PCT/US2016/022573, dated Sep. 29, 2017, 8 pages.

International Search Report and Written Opinion for Application No. PCT/US2016/022573, dated Jun. 2, 2016, 13 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP19209515.6, dated Feb. 28, 2020, 7 pages.

US 10,660,716 B2

SYSTEMS AND METHODS FOR RENDERING ONSCREEN IDENTIFICATION OF INSTRUMENTS IN A TELEOPERATIONAL MEDICAL SYSTEM

RELATED APPLICATIONS

This patent application is the continuation of U.S. patent application Ser. No. 15/558,466 filed Sep. 14, 2017, which is the U.S national phase of International Application No. PCT/US2016/022573, filed Mar. 16, 2016, which designated the U.S. and claims priority to and the benefit of the filing date of U.S. Provisional Patent Application No. 62/134,294, entitled "SYSTEMS AND METHODS FOR RENDERING ONSCREEN IDENTIFICATION OF INSTRUMENTS IN A TELEOPERATIONAL MEDICAL SYSTEM," filed Mar. 17, 2015, which are incorporated by reference herein in their entireties.

FIELD

The present disclosure is directed to systems and methods for performing a teleoperational medical procedure and more particularly to systems and methods for displaying information about teleoperational instruments used in a surgical environment.

BACKGROUND

Minimally invasive medical techniques are intended to reduce the amount of tissue that is damaged during invasive medical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments. Imaging instruments provide a user with a field of view within the patient anatomy. Some minimally invasive medical tools and imaging instruments may be teleoperated or otherwise computer-assisted. In a teleoperational medical system, instruments may be difficult to see, whether due to small instrument size, proximity to the edge of the field of view, or obstruction by tissue. A clinician operating the teleoperational system may also have difficulty keeping track of which instruments are under which operator controls. Systems and methods are needed to provide a clinician with information about the instruments under the clinician's control to reduce the risk of clinician error.

SUMMARY

The embodiments of the invention are summarized by the claims that follow below.

In one embodiment, a teleoperational assembly includes an operator control system and a plurality of manipulators configured to control the movement of medical instruments in a surgical environment. The manipulators are teleoperationally controlled by the operator control system. The system further includes a processing unit configured to display an image of a field of view of the surgical environment, project the position of distal end portions of the medical instruments into the image's coordinate space, determine initial positions for badges associated with the distal end portions of each medical instrument, evaluate a display factor for each badge based on its initial position, and determine a final display position for each badge in the image's coordinate space based on the display factor.

In another embodiment, an image of a field of view of a surgical environment is displayed. The image is obtained by an imaging instrument and contains images of distal ends of medical instruments. The medical instruments are coupled to manipulators of a teleoperational assembly. The positions of the distal ends of the medical instruments are projected into the image's coordinate space, the initial positions of badges associated with the distal ends of the medical instruments are determined, a display factor is evaluated for each badge based on their initial positions, and the final display position of each badge in the image's coordinate space is determined based on their display factors.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1A:
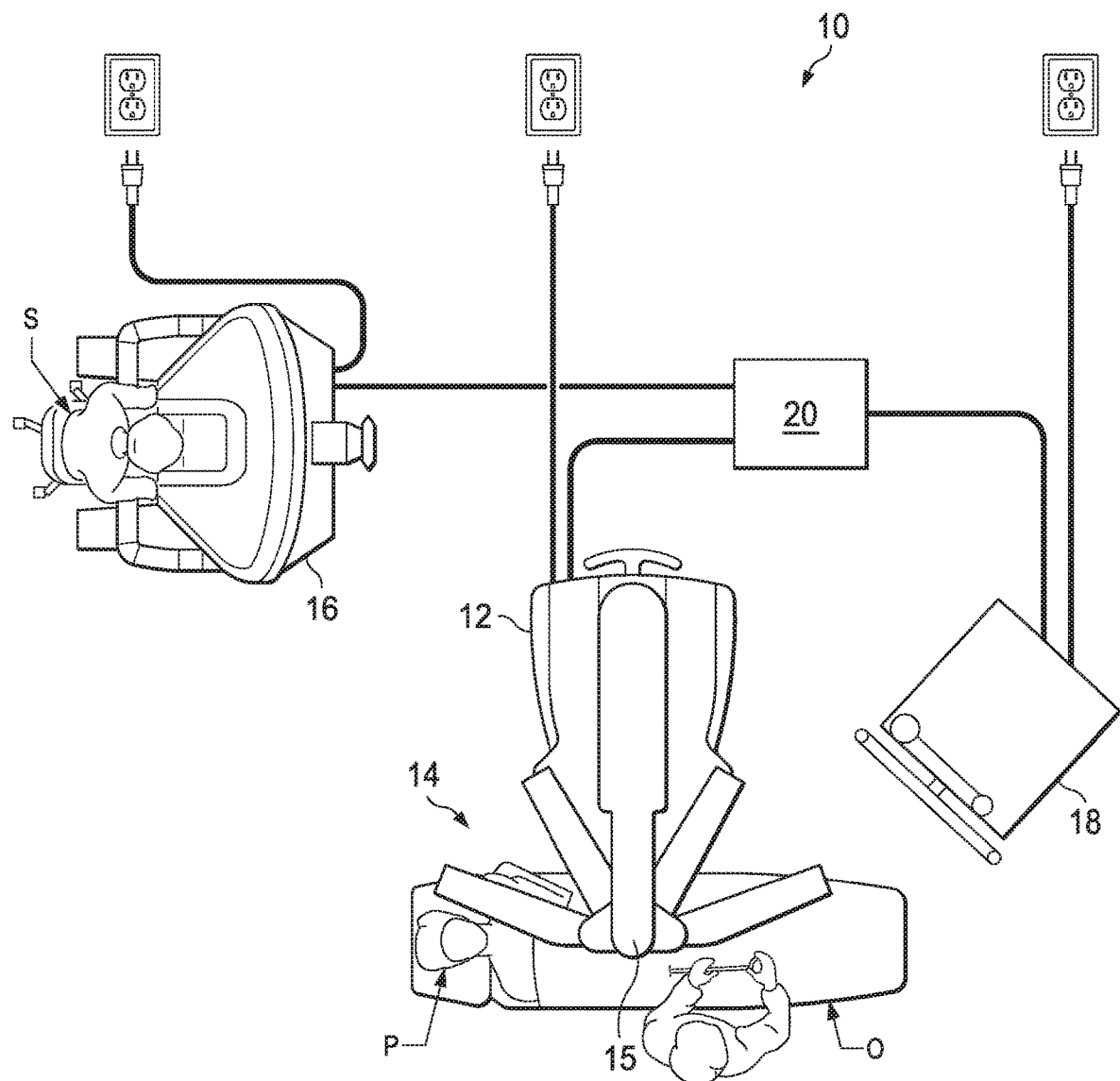
FIG. 1A is a schematic view of a teleoperational medical system, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperational medical system 10 generally includes a teleoperational assembly 12 mounted to or near an operating table O on which a patient P is positioned. The teleoperational assembly 12 may be referred to as a patient side cart. A medical instrument system 14 and an endoscopic imaging system 15 are operably coupled to the teleoperational assembly 12. An operator input system 16 allows a surgeon or other type of clinician S to view images of or representing the surgical site and to control the operation of the medical instrument system 14 and/or the endoscopic imaging system 15.

The operator input system 16 may be located at a surgeon's console, which is usually located in the same room as operating table O. It should be understood, however, that the surgeon S can be located in a different room or a completely different building from the patient P. Operator input system 16 generally includes one or more input control device(s) for controlling the medical instrument system 14. The input control device(s) may include one or more of any number of a variety of devices, such as hand grips, joysticks, trackballs, data gloves, trigger-guns, hand-operated controllers, voice recognition devices, touch screens, pedals, body motion or presence sensors, eye-gaze tracking devices and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 12 supports and manipulates the medical instrument system 14 while the surgeon S views the surgical site through the console 16. An image of the surgical site can be obtained by the endoscopic imaging system 15, such as a stereoscopic endoscope, which can be manipulated by the teleoperational assembly 12 to orient the endoscope 15. Optionally, an electronics cart 18 can be used to process the images of the surgical site for subsequent display to the surgeon S through the surgeon's console 16. The number of medical instrument systems 14 used at one time will generally depend on the diagnostic or surgical procedure and the space constraints within the operating room among other factors. The teleoperational assembly 12 may include a kinematic structure of one or more non-servo controlled links (e.g., one or more links that may be manually positioned and locked in place, generally referred to as a set-up structure) and a teleoperational manipulator. The teleoperational assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 10 also includes a control system 20. The control system 20 includes at least one memory and at least one processor (not shown), and typically a plurality of processors, for effecting control between the medical instrument system 14, the operator input system 16, and an electronics system 18. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The teleoperational medical system 10 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 1B:
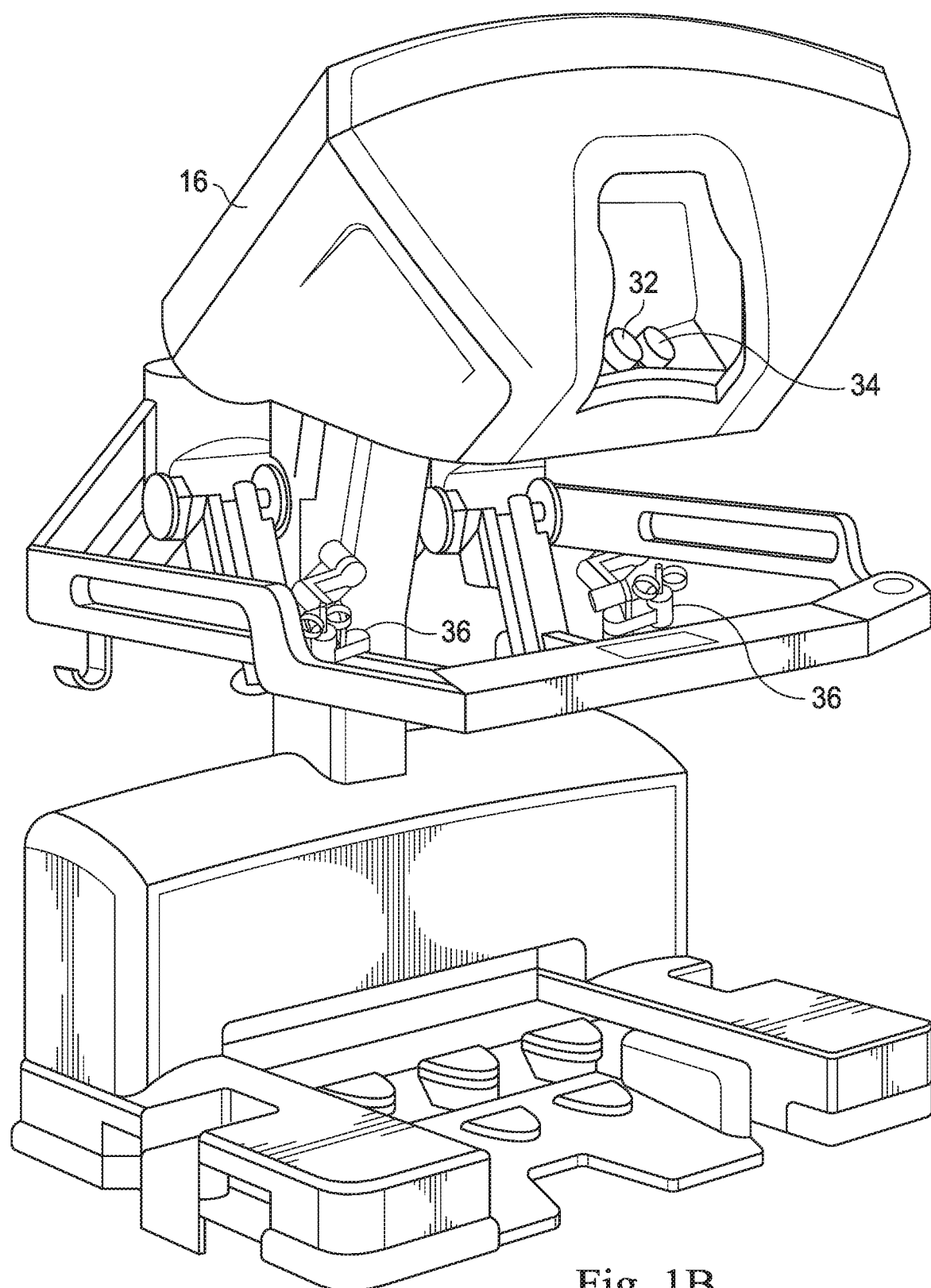
FIG. 1B is a perspective view of a surgeon's control console for a teleoperational medical system, in accordance with many embodiments.

FIG. 1B is a perspective view of the surgeon's console 16. The surgeon's console 16 includes a left eye display 32 and a right eye display 34 for presenting the surgeon S with a coordinated stereo view of the surgical site that enables depth perception. The console 16 further includes one or more input control devices 36, which in turn cause the teleoperational assembly 12 to manipulate one or more instruments or the endoscopic imaging system. The input control devices 36 can provide the same degrees of freedom as their associated instruments 14 to provide the surgeon S with telepresence, or the perception that the input control devices 36 are integral with the instruments 14 so that the surgeon has a strong sense of directly controlling the instruments 14. To this end, position, force, and tactile feedback sensors (not shown) may be employed to transmit position, force, and tactile sensations from the instruments 14 back to the surgeon's hands through the input control devices 36.

Figure 1C:
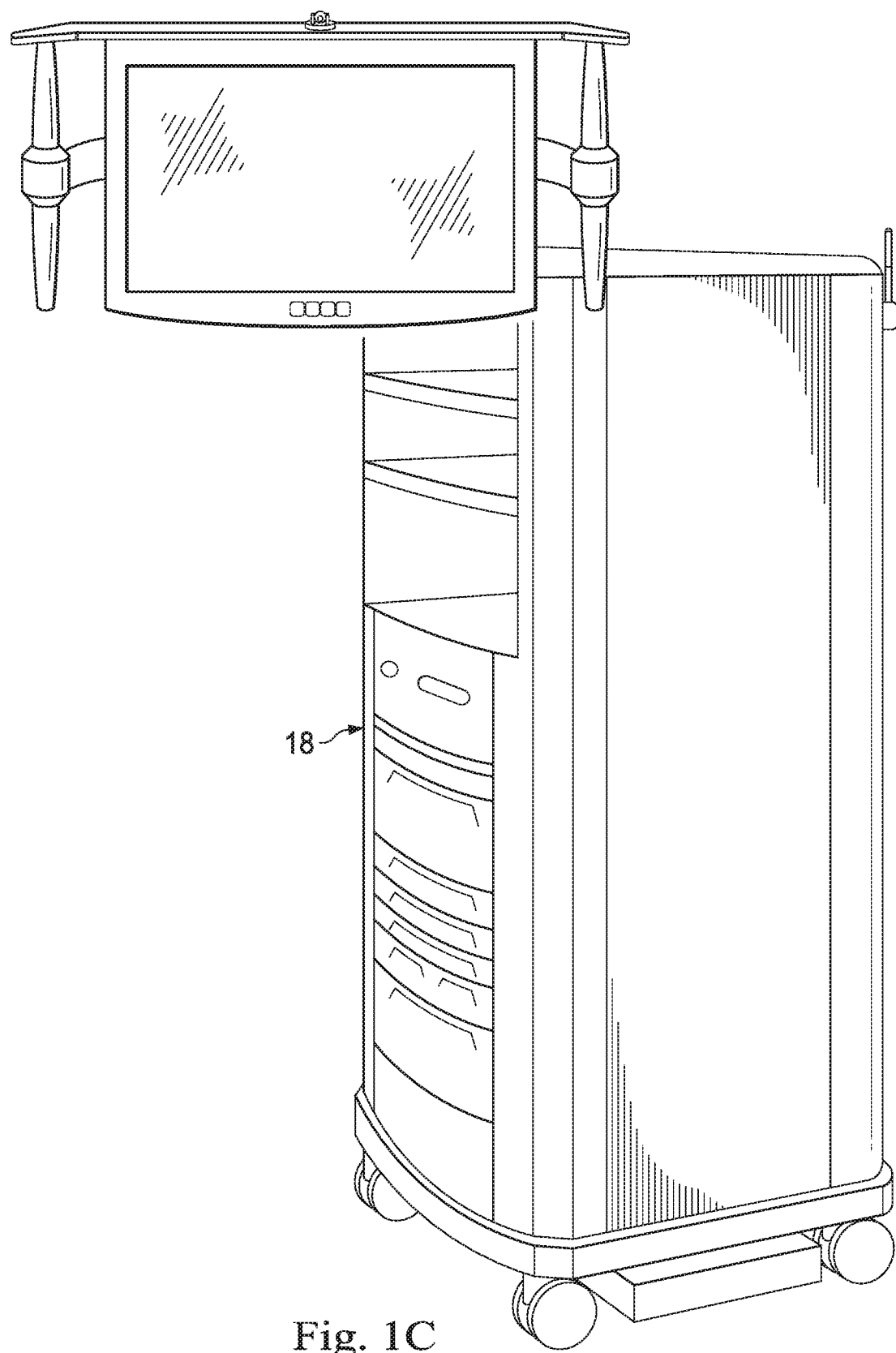
FIG. 1C is a perspective view of a teleoperational medical system electronics cart, in accordance with many embodiments.

FIG. 1C is a perspective view of the electronics cart 18. The electronics cart 18 can be coupled with the endoscope 15 and can include a processor to process captured images for subsequent display, such as to a surgeon on the surgeon's console, or on another suitable display located locally and/or remotely. For example, where a stereoscopic endoscope is used, the electronics cart 18 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. The electronics cart 18 may also include a display monitor and components of the control system 20.

Figure 1D:
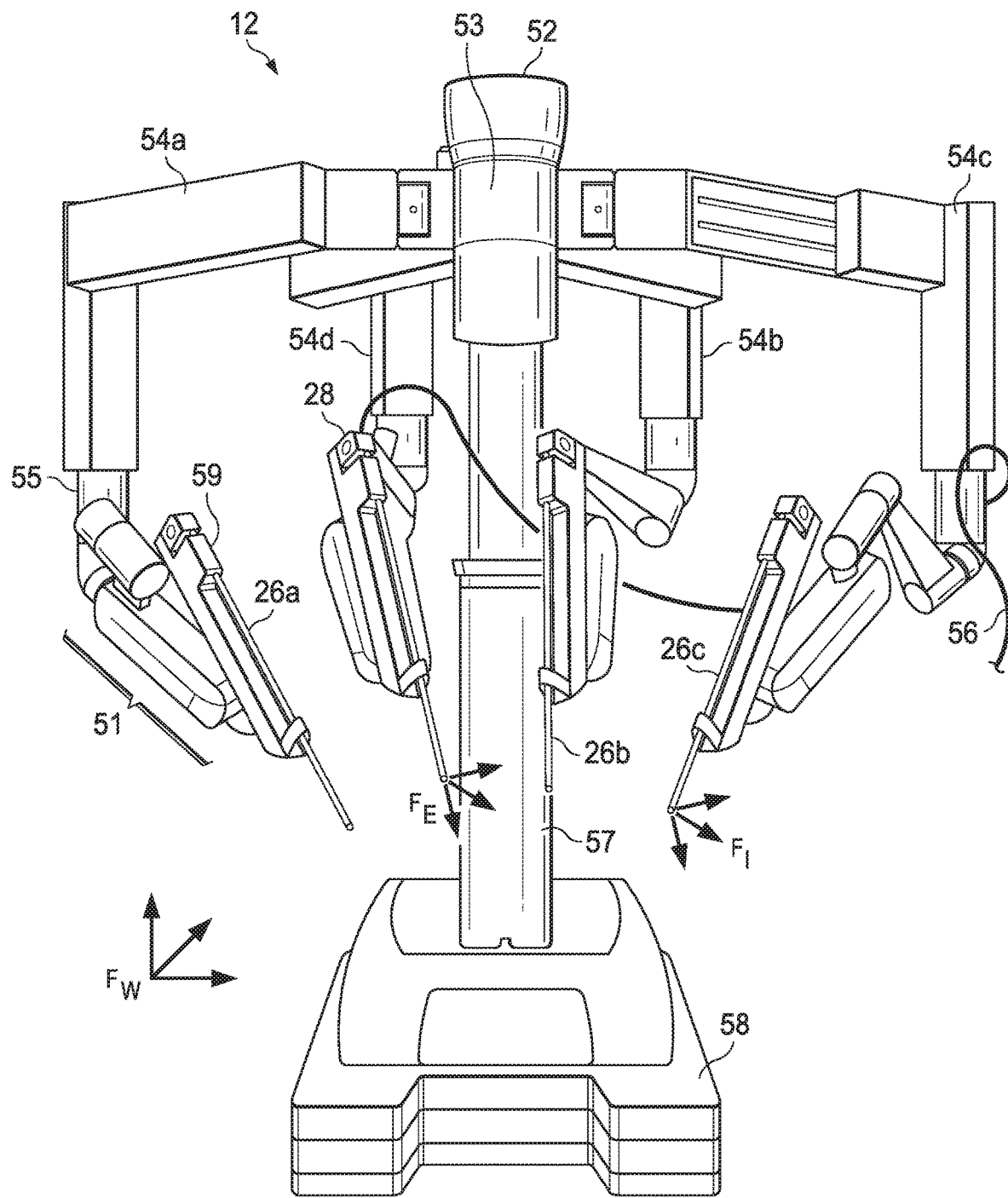
FIG. 1D is a perspective view of a patient side cart, according to one example of principles described herein.

FIG. 1D is a perspective view of one embodiment of a teleoperational assembly 12 which may be referred to as a patient side cart. The patient side cart 12 shown provides for the manipulation of three surgical tools 26a, 26b, 26c (e.g., instrument systems 14) and an imaging device 28 (e.g., endoscopic imaging system 15), such as a stereoscopic endoscope used for the capture of images of the site of the procedure. The imaging device may transmit signals over a cable 56 to the electronics cart 18. Manipulation is provided by teleoperative mechanisms having a number of joints. The imaging device 28 and the surgical tools 26a, 26b, 26c can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28. The teleoperational assembly 12 is located in a world coordinate system or frame $F_W$. The distal tip of each medical instrument 26a, 26b, 26c defines a respective instrument coordinate system or frame $F_I$. The distal tip of the imaging device 28 defines a coordinate system or frame $F_E$.

The patient side cart 12 includes a drivable base 58. The drivable base 58 is connected to a telescoping column 57, which allows for adjustment of the height of arms 54a, 54b, 54c, and 54d. Arm 54a may be known and/or labeled in the surgical environment as "Arm 1." Arm 54b may be known and/or labeled in the surgical environment as "Arm 2." Arm 54c may be known and/or labeled in the surgical environment as "Arm 3." Arm 54d may be known and/or labeled in the surgical environment as "Arm 4." The arms 54a may include a rotating joint 55 that both rotates and moves up and down. Arm 54a connects to a manipulator arm portion 51. The manipulator arm portions 51 may connect directly to the medical instrument 26a via a manipulator spar 59. Each of the other arms 54b, 54c, 54d may have a similar configuration to arm 54a. Each of the arms 54a, 54b, 54c, 54d may be connected to an orienting platform 53. The orienting platform 53 may be capable of 360 degrees of rotation. The patient side cart 12 may also include a telescoping horizontal cantilever 52 for moving the orienting platform 53 in a horizontal direction. The manipulator arm portion 51 may be teleoperable. The arms 54a, 54b, 54c, 54d may be teleoperable or not. In embodiments in which the arm 54 is not teleoperable but the manipulator arm is, the arm 54 is positioned as desired before the surgeon begins operation with the system 10. Note that while arms 54 (and associated manipulator arm portions 51) are depicted and described as being part of a single patient side cart 12 for exemplary purposes, in various other embodiments, arms 54 and/or manipulator arm portions 51 (or additional arms 54 and/or manipulator arm portions 51) can be discrete structures (e.g., separate table-, ceiling-, and/or floor-mounted arms).

Endoscopic imaging systems (e.g., systems 15, 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Endoscopes may be provided with different viewing angles including a 0° viewing angle for forward axial viewing or viewing angles between 0°-90° for forward oblique viewing. Digital image based endoscopes have a "chip on the tip" design in which a distal digital sensor such as a one or more charge-coupled device (CCD) or a complementary metal oxide semiconductor (CMOS) device store image data. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic instruments employ stereo cameras to capture stereo images of the patient anatomy in the camera's field of view.

The stereo images of the imaging system field of view may be seen by a clinician through the eye displays 32, 34. In addition to the patient tissue, the field of view may also include the distal ends of the medical instruments and any accessories used in performing the surgical procedure. To perform the procedure, a clinician recognizes an association between an instrument in the field of view and the input control device controlling that instrument from the control console. The clinician may make this association by, for example, referring to alphanumeric text, symbols, or other information located at the periphery of the viewed image. To view this information, however, the clinician's focus must move away from the central portion of the display and distal tips of the instruments to the periphery of the image. Alternatively, the clinician may make the association by moving an input control device and observing the corresponding instrument movement in the image. This may be time consuming and disruptive to the flow of the surgical procedure. To aid the clinician in associating the input control devices 36 with the instruments visible in the field of view, information about an input control device may be presented in graphical form and co-located with the instrument it controls. Co-locating the association information with the instrument allows the clinician to quickly associate control devices with instruments while maintaining focus on the surgical area of interest.

Figure 2A:
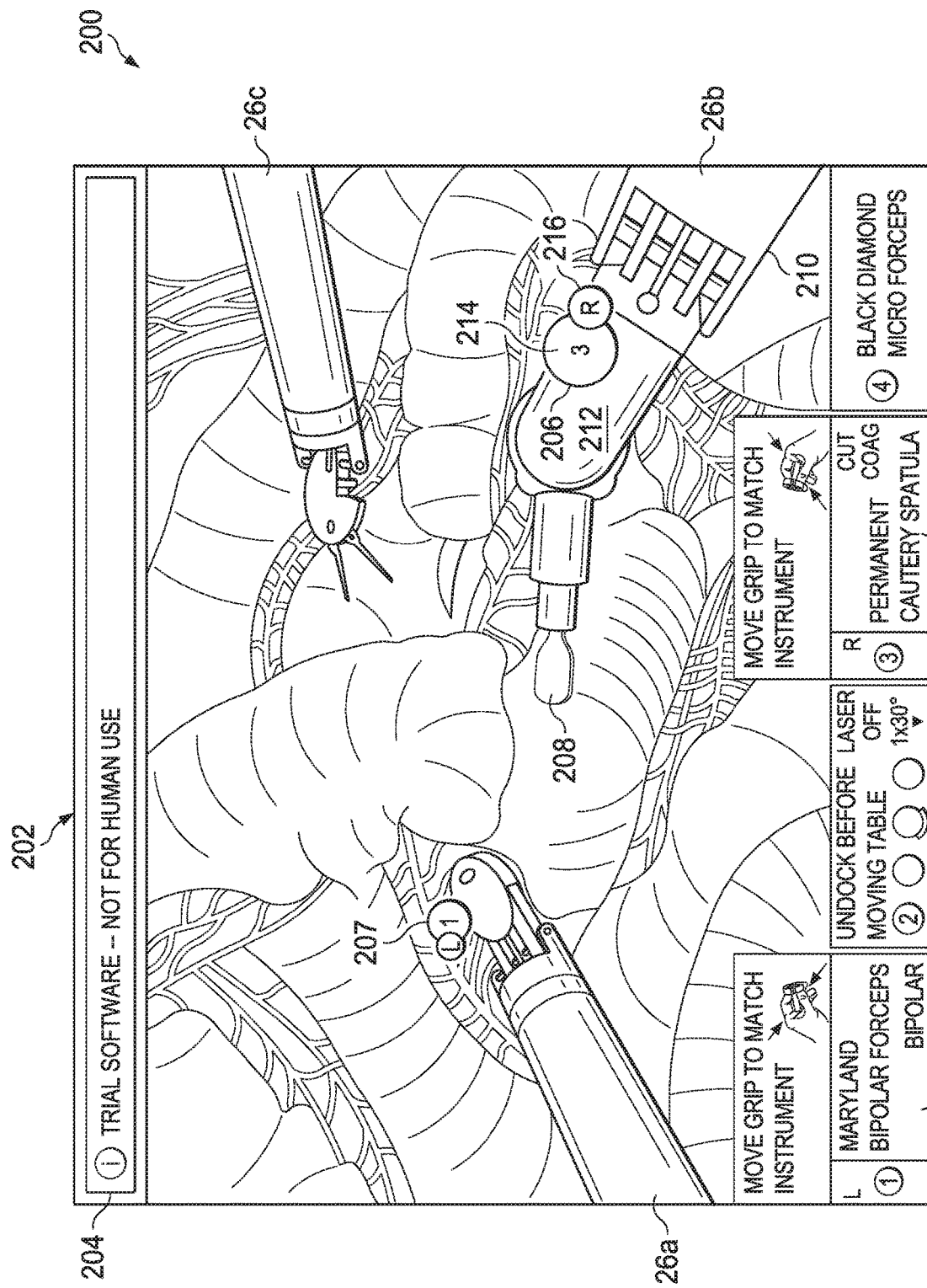
FIG. 2A illustrates a field of view of a surgical workspace with at least one medical instrument visible in the field of view, the instrument having a badge associated with it and containing association information pertaining to the instrument.

FIG. 2A illustrates a surgical environment 200 within the patient P. An imaging instrument (e.g., imaging instrument 28) is used to display an image 202 of the imaging instrument's field of view within the surgical environment 200. The image 202 may be a three dimensional image obtained by a stereoscopic endoscope and generated as a composite image of the images visible to a user through right and left eye displays. The field of view includes a distal end portion of instrument 26a, a distal end portion of instrument 26b, and a distal end portion of instrument 26c. The image 202 also includes information fields 204 located at the periphery of the image which may include instructions to the clinician, warnings, instrument identification information, status information, or other information relevant to the surgical procedure. To assist the clinician in performing the surgical procedure using the system 10, various pieces of information are superimposed on the image 202. In this embodiment, a badge 206 contains association information related to the medical instrument 26b, such as a numerical identifier of the arm 54b (e.g. Arm "3") to which the instrument is coupled. The badge 206 is displayed proximate to the medical instrument 204 so that the clinician can easily tell that the association information pertains to the medical instrument 26b. In some embodiments, the badge may also include association information including the type of medical instrument, the state of the medical instrument (e.g. cauterizer charging/ready) or the like. Methods for creating and displaying the badge 206 are described in further detail below, with reference to FIGS. 8-11. In various embodiments, the badge may be circular, oval, square or any suitable shape. In various embodiments, a badge may have colors, outlines, shapes, or other features to identify or distinguish badges from one another.

The distal end portion of the medical instrument 26b visible in the field of view includes an end effector tip 208, a shaft 210, and a joint region 212 between the shaft and end effector tip. In some embodiments, a default location for placement of the badge 206 is superimposed over the joint region 212. In other embodiments, the default location for placement of the badge 206 may be on the end effector tip 208 or the shaft 210. In other embodiments, the badge 206 is displayed adjacent to the distal end portion. The default location for the badge may depend upon the size of the distal end portion of the medical instrument 26b in the field of view. For example, if the image is closely zoomed in (e.g., FIG. 3F), and the end effector occupies a large portion of the image, the badge may be located on a proximal portion of one of the end effector jaws without obstructing the view at the distal end of the jaws. If, however, the image is zoomed out and the end effector jaws are relatively small in the image, the badge may be located on the joint region or the shaft to avoid obscuring the jaws. The placement of the badge 206 allows the clinician to receive the association information while remaining focused on the instruments and the tissue manipulated by the instruments. The placement of the badge 206 also avoids obscuring objects in the field of view that need to be observed by the clinician.

In some embodiments the badge 206 has a central portion 214 as well as an orbiting portion 216. The central portion 214 and orbiting portion 216 may contain different pieces of association information. For example, as shown in FIG. 2, the central portion 214 includes a number indicating the arm 54b (e.g. Arm "3") to which the medical instrument 26b is attached. In various embodiments, orbiting portion 216 contains association information related to the control device used by the clinician to control the medical instrument 26b. This association information may be, for example, an indication of whether a right (e.g., "R") or left (e.g., "L") hand-operated input control device is currently in control of the medical instrument 26b to which badge 206 is associated.

The orbiting portion 216 of the badge 206 may move circumferentially relative to the central portion 214 of badge. The circumferential location of the orbiting portion 216 indicates the rotational position of the control device, letting the clinician know where their hand on the control device is positioned relative to the medical instrument 26b which they are controlling. The function of the orbiting portion 216 is shown in greater detail in FIGS. 3A-3F.

A badge 207 is located proximate to the instrument 26a and has similar features and attributes as badge 206. Badge 207 contains association information related to the medical instrument 26a, such as a numerical identifier of the arm 54a (e.g. Arm "1") to which the instrument is coupled. In this embodiment and at this phase of the surgical procedure, instrument 26c is not presently under control of an input control device. Therefore, a badge is not located proximate to the instrument 26c. In alternative embodiments, badge information may be provided for the instrument 26c indicating the numerical identifier of the arm 54c (e.g., Arm "4"), but the fact that the instrument is not presently under control of an input device may be indicated by color, symbol, or other indication.

Figure 2B:
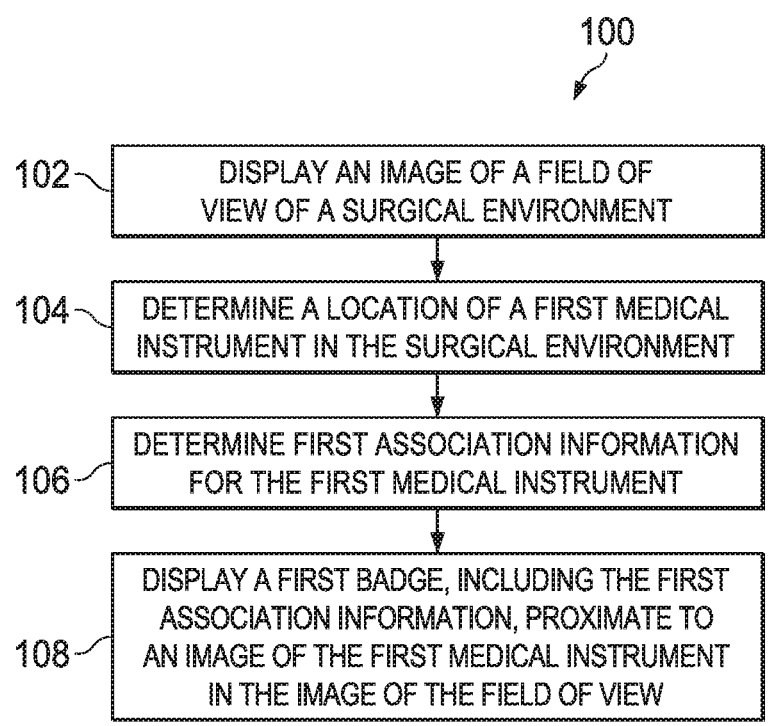
FIG. 2B is a flowchart illustrating a method for operating a teleoperational medical system.

FIG. 2B illustrates a method 100 of operating a teleoperational system to perform a surgical procedure. At a process 102, the method comprises displaying an image 202 of a field of view of a surgical environment. At a process 104, a location of a medical instrument 26a in the surgical environment is determined. At a process 106, association information for the medical instrument 26a is determined. The association information includes information about the teleoperational manipulator to which the medical instrument 26a is coupled and/or about the operator input control that controls the medical instrument. At a process 108, a badge is displayed proximate to an image of the medical instrument 26a in the image 202 of the field of view. The badge includes the association information.

Figure 3A:
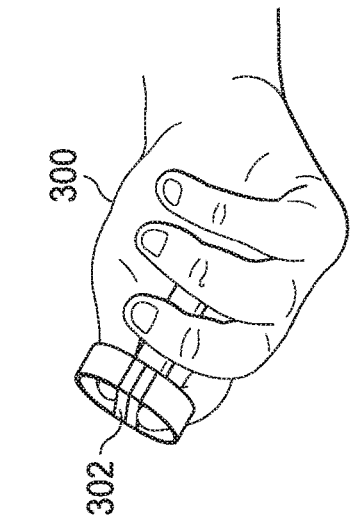
FIGS. 3A-3C illustrate input control devices and user hand positions that correspond to association information badge arrangements as shown in FIGS. 3D-3F.
Figure 3B:
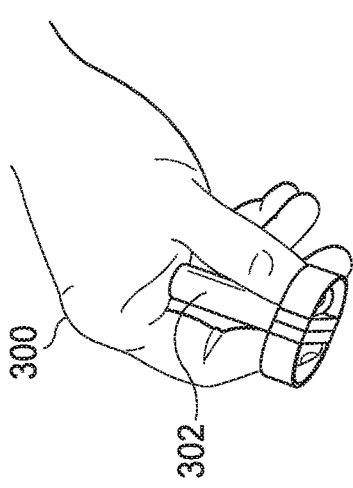
Figure 3C:
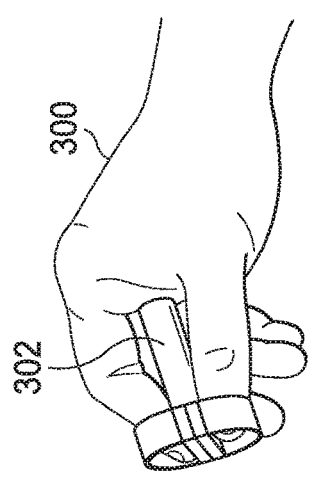
Figure 3D:
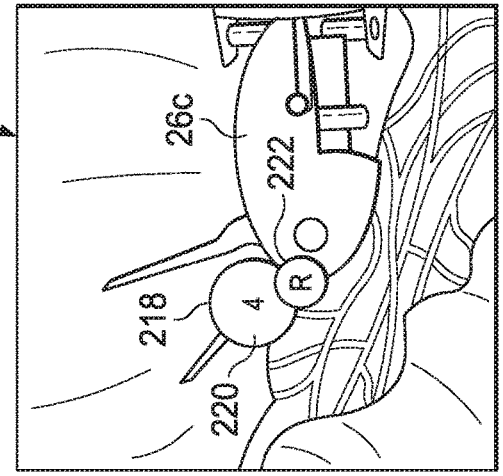
FIGS. 3D-3F illustrate various arrangements for an orbiting portion of an association information badge.
Figure 3E:
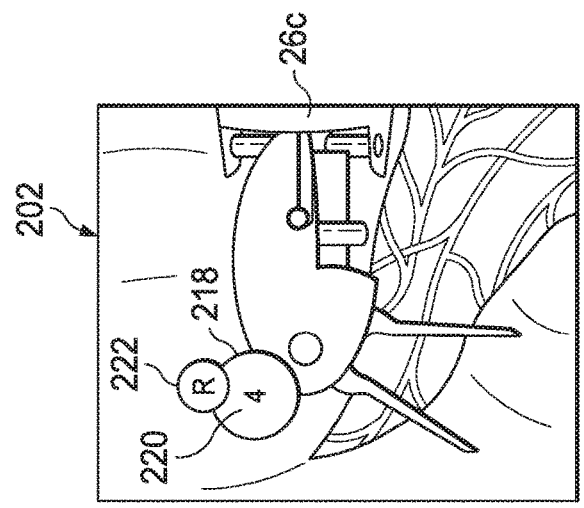
Figure 3F:
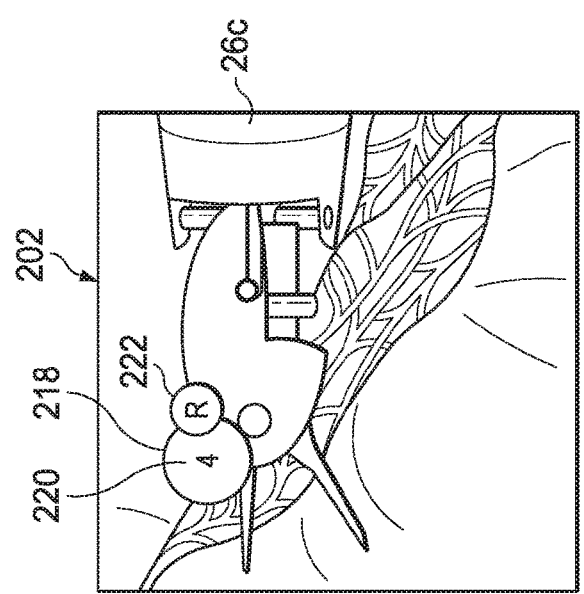

FIG. 3A-3C illustrates a clinician's right hand 300 controlling an input control device 302 (i.e., an input control device 36). The input control device 302 controls the medical instrument 26c. As shown in FIG. 3A, from the clinician's perspective, the input control device 302 extends toward the right. Hand association information including hand identity (right or left) and the orientation of the hand may be conveyed to the clinician via the badge. Although this control association information is described in terms of a human hand, similar association information may be provided where control is delivered by foot pedals, eye gaze trackers, voice commands, or other clinician controls. As shown in FIG. 3D, hand association information about the control device 302 of FIG. 3A is conveyed visually to the clinician in the image 202 by orienting an orbiting portion 222 of a badge 218 to the right (e.g. at about a 3 o'clock position) relative to the central portion 220 of the badge. The orbiting portion 222 displays an "R" to indicate that the right-hand control device 302 is being used to control the medical device 26c. As shown in FIG. 3B, from the clinician's perspective, the input control device extends upward, approximately 90 degrees from the position in FIG. 3A. As shown in FIG. 3E, this orientation information about the control device 302 of FIG. 3B is conveyed visually to the clinician in the image 202 by orienting the orbiting portion 222 of the badge 218 upward (e.g. at about a 12 o'clock position) relative to the central portion 220 of the badge. As shown in FIG. 3C, from the clinician's perspective, the input control device extends downward, approximately 90 degrees from the position in FIG. 3A. As shown in FIG. 3F, this orientation information about the control device 302 of FIG. 3C is conveyed visually to the clinician in the image 202 by orienting the orbiting portion 222 of the badge 218 downward (e.g. at about a 6 o'clock position) relative to the central portion 220 of the badge.

In some alternative embodiments, hand association information may be provided as the an illustration or 3D model of a hand. The illustration or model portrays a left or right hand according to whether a left-hand or right-hand control device is being used to control the associated medical device. Similar to the orbiting portion 222 in FIGS. 3D-3F, as the orientation of the control device changes the position of the illustration or model changes accordingly to visually convey information about the new orientation of the control device to the clinician. The properties and features described for any of the badges in this disclosure may apply to any of the other badges in this disclosure.

Figure 4A:
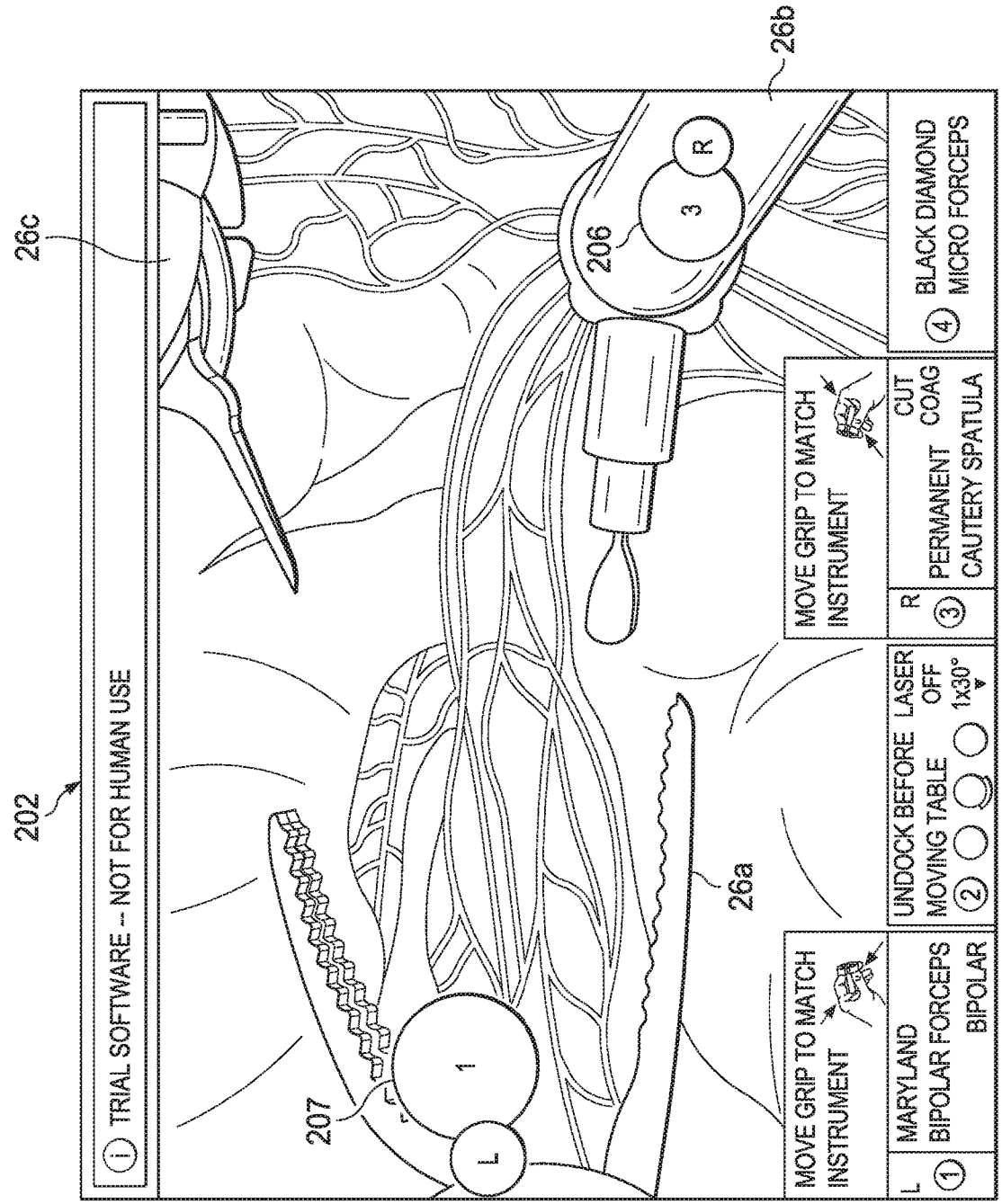
FIGS. 4A-4B illustrate the size-changing behavior of the association information badge as the associated instrument moves toward and away from the imaging device.
Figure 4B:
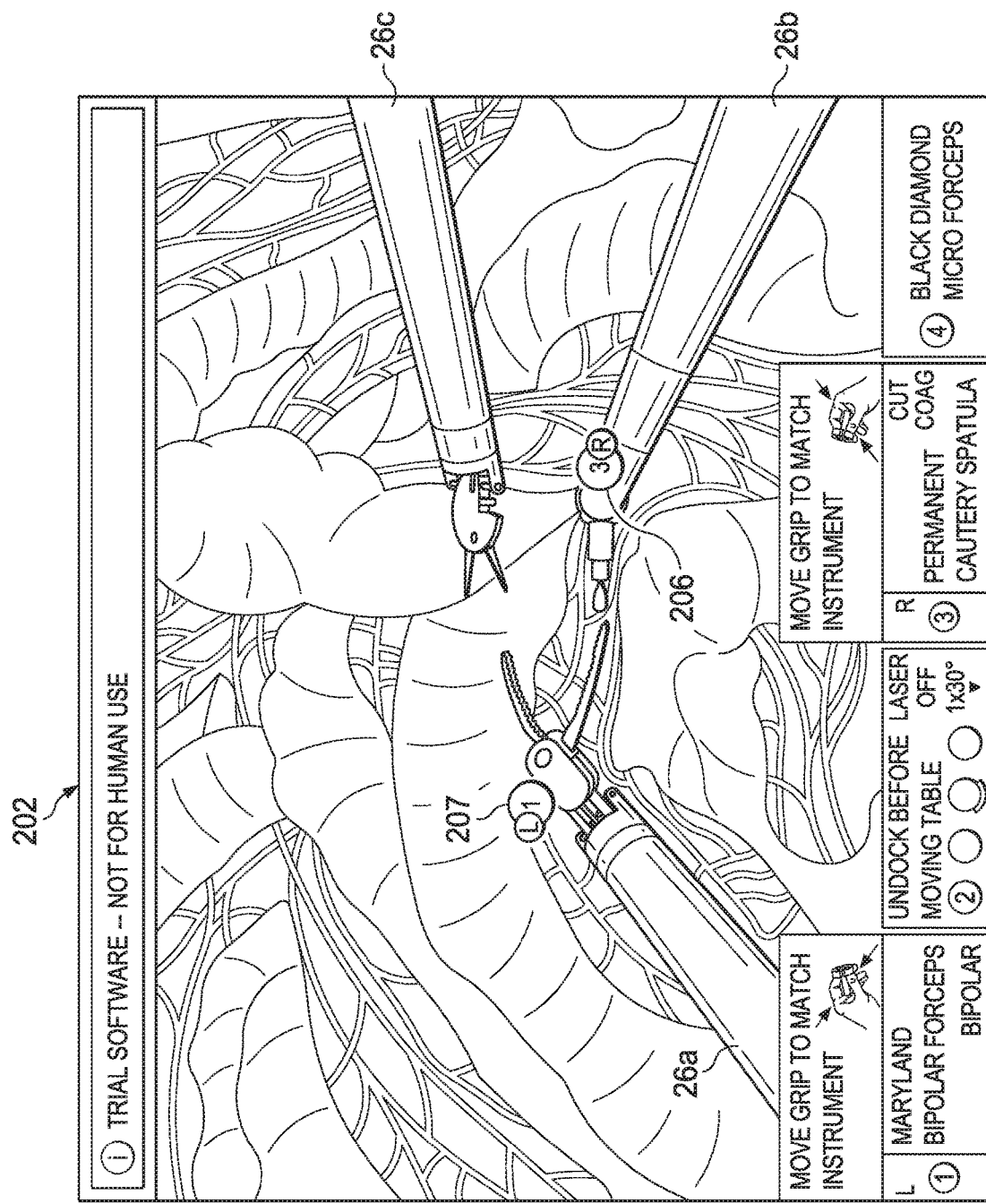

Referring now to FIGS. 4A-4B, there is shown further behavior of the badge 206 as the imaging device is moved or zoomed within the surgical environment. In an embodiment shown in FIG. 4A, the imaging instrument is moved or zoomed in toward the medical instruments 26a, 26b, 26c. As the medical instruments 26a, 26b, 26c appear larger in the field of view and the image 202, the badges 206, 207 become larger, changing size to appear as if they are located at the same depth in the field of view as the distal end portions of the instruments. In FIG. 4B, as the imaging instrument is moved further away or zoomed out from the medical instruments 26a, 26b, 26c, the badges 206, 207 become smaller, again changing to appear as if they are located at the same depth in the field of view as the distal end portions of the instruments. In some embodiments there is a limit on the maximum and minimum size of the badges 206, 207 to prevent them from becoming unreadable. Further detail about the badge positions and sizes are provided below in the description for FIGS. 8-11. The size of the badges 206, 207 may also impart additional information to the clinician such as a distance between the medical instruments 26a, 26b and the imaging device. This may be helpful because different types of medical instruments vary in size, and a small instrument close to the imaging device could appear to be the same size as a large instrument far away from the imaging device.

Figure 5A:
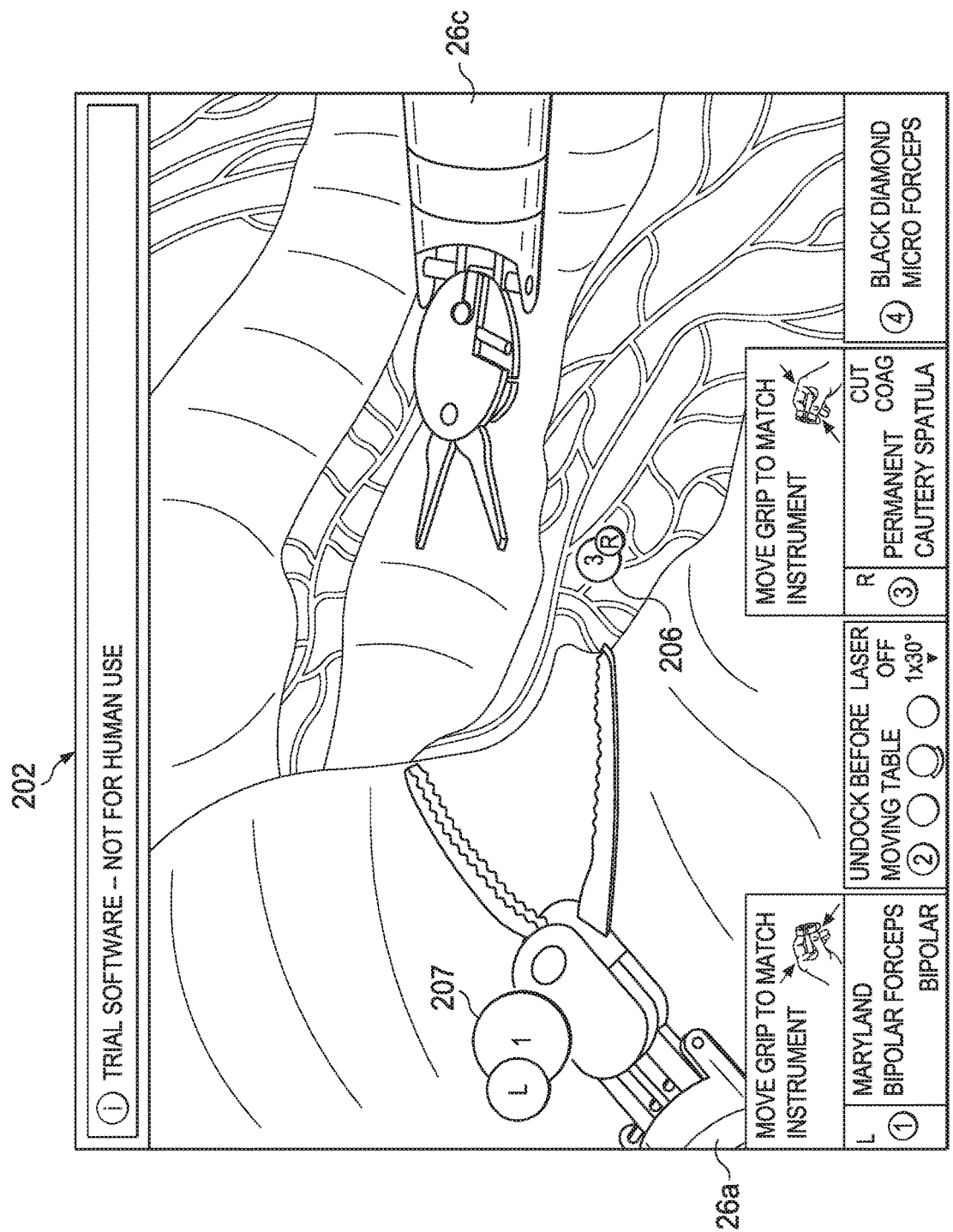
FIGS. 5A-5B illustrate how the association information badge remains visible when the associated medical instrument is obstructed from view.
Figure 5B:
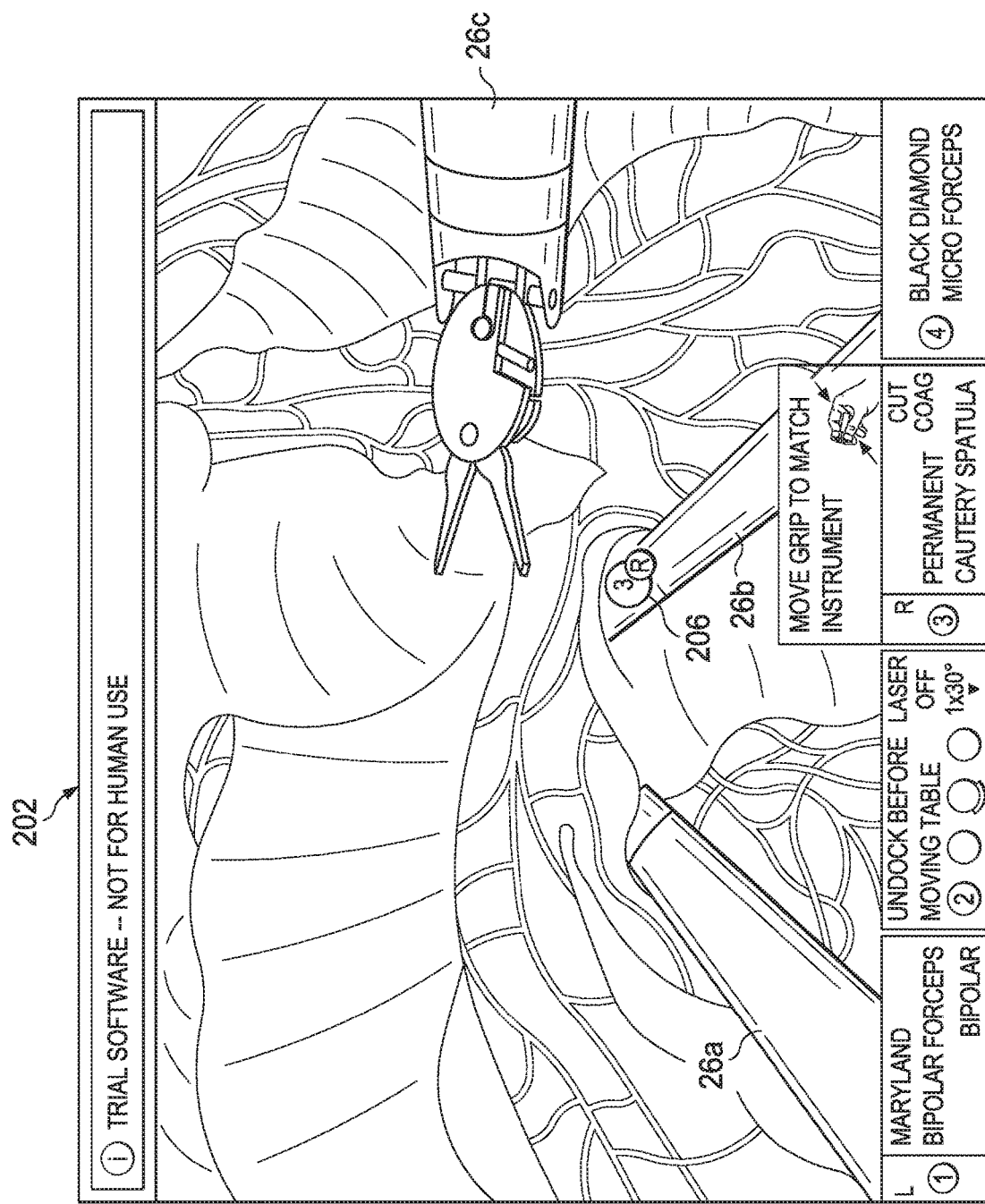

Since the badges 206, 207 are superimposed on the image 202, they may appear on the display even if the view of the medical instruments 26a, 26b is obstructed by tissue, other instruments, or the like. As shown in FIG. 5A badge 206 remains visible even as the associated instrument 26b is hidden behind tissue. The presence of the badge 206 substantially offset from and at a different apparent size and depth than other instruments 26a, 26c visible in the field of view indicates to the clinician that the instrument 26b associated with the badge is occluded. The badge 206 allows the occluded instrument 26b to be found as shown in FIG. 5B. In FIG. 5B the tissue has been moved and the medical instrument 26b to which badge 206 is attached have become visible in the field of view.

The teleoperational medical system 10 may have multiple operational states for each instrument. These may include an active state, wherein a medical instrument is under the control of an input control device such that the clinician is actively controlling the medical instrument. In a disengaged state, a medical instrument is not under the control of an input control device and remains stationary, locked in place by the manipulator arm to which it is coupled. The system may also have an engagement state in which the user is prompted to engage or take control of the medical instrument via the associated input control device. In some embodiments, the badges are displayed when the teleoperational medical system is in the engagement state for a particular instrument. For example, in FIG. 4A, instruments 26a and 26b are in an engagement state in which the user is prompted by the badge information to take control of instrument 26a on Arm 1 with the left ("L") input control device and to take control of instrument 26b on Arm 3 with the right ("R") input control device. Instrument 26c is in a disengaged state and thus, a badge is not presented for the instrument. During the active state, the badges may remain visible in the image or may be removed to avoid distraction to the clinician. Presenting the badges in the engagement state allows the clinician to recognize the association information and location of each instrument within the field of view 202 before taking control of any of the medical instruments. For example, the location of the badge may be used to determine if any medical instruments are obstructed from view by tissue before taking control of the instrument. Additionally, the association information contained within the badge may give the clinician information that allows him to choose which medical instrument to take control of to perform a desired procedure. Further, the information given by the orbiting portion of the badge may tell the clinician how to position the input control device to match position with the orientation of the medical instrument before taking control. In some embodiments, the system may require the clinician to match this position before allowing a change of state from engagement to active.

Figure 6A:
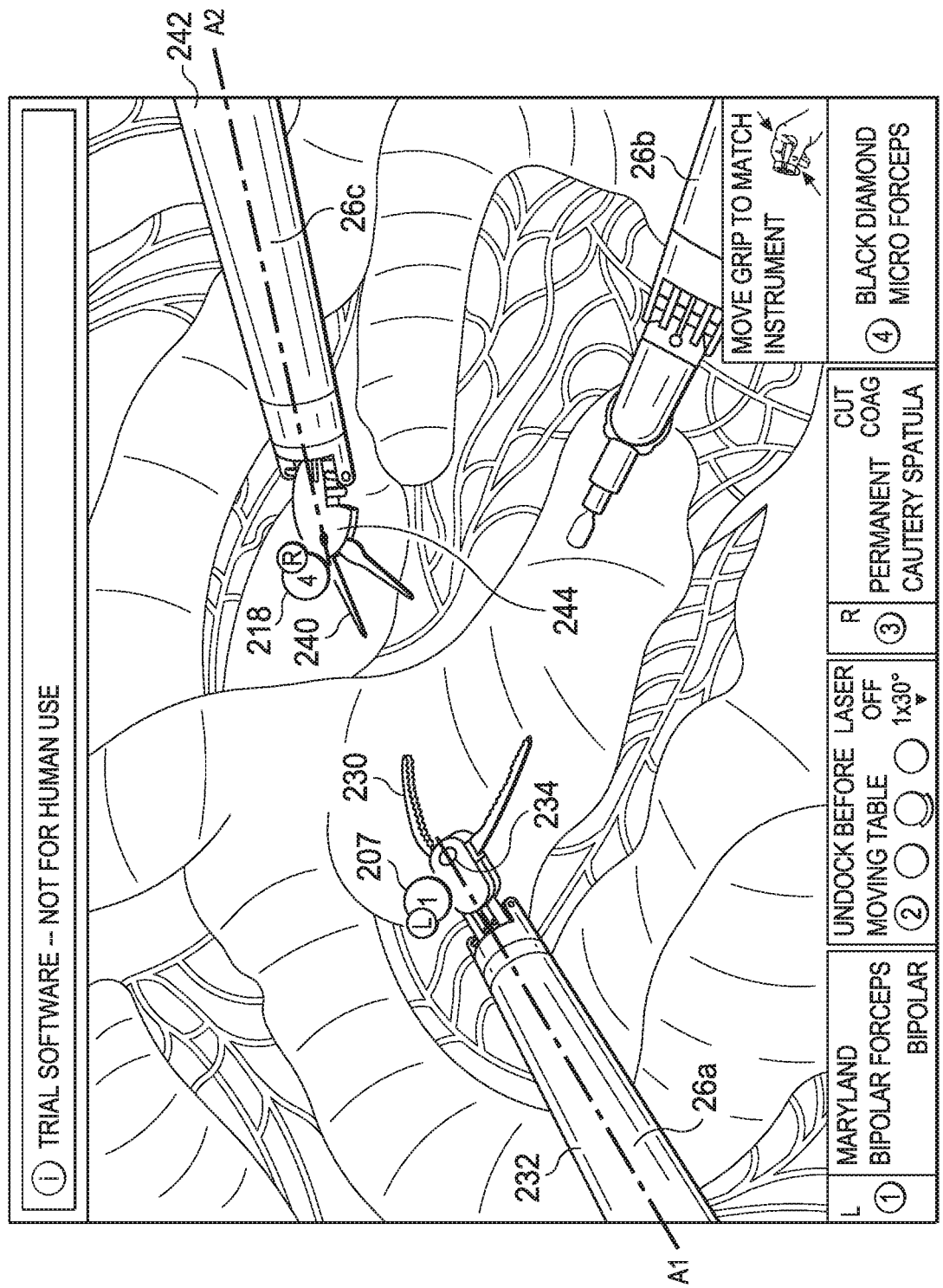
FIGS. 6A-6B illustrate the adjustment of the association information badge when medical instruments are in close proximity.
Figure 6B:
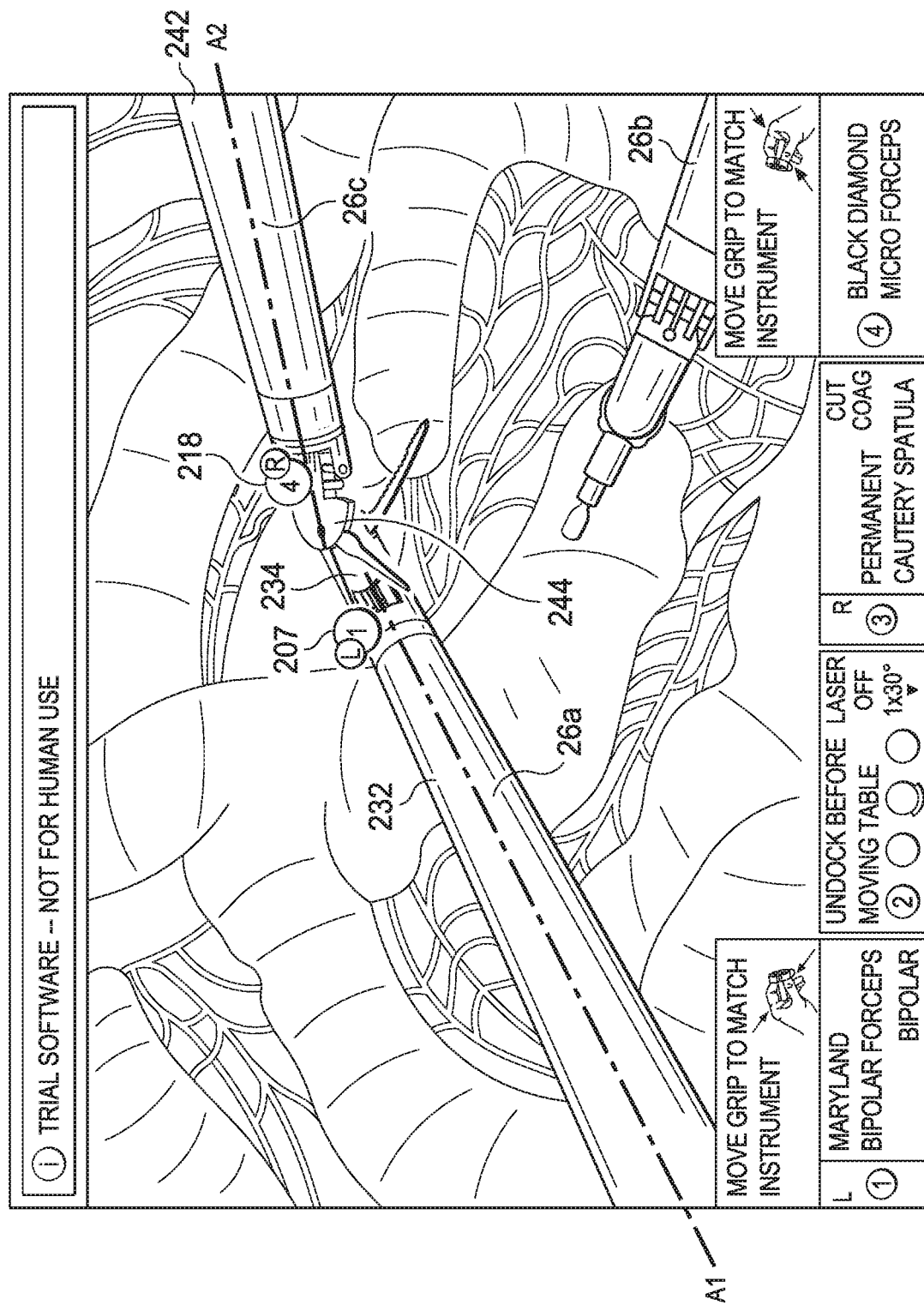

Referring now to FIGS. 6A-6B, the distal end portion of the medical instrument 26a visible in the field of view includes an end effector tip 230, a shaft 232, and a joint region 234 between the shaft and end effector tip. The distal end portion of the medical instrument 26c visible in the field of view includes an end effector tip 240, a shaft 242, and a joint region 244 between the shaft and end effector tip. As shown in FIG. 6A and previously described, a default location for placement of the badge 207 is superimposed over the joint region 234. A default location for placement of the badge 218 is superimposed over the joint region 244. In FIG. 6A, the instrument distal end portions are spaced apart and easily distinguishable from each other, consequently, the badges 207 and 218 are clearly readable and clearly associated with medical instruments 26a and 26c, respectively. FIG. 6B illustrates the case where the distal end portions of instruments 26a and 26c are overlapping or in very close proximity in the image 202. If allowed to remain in their default locations, the badges 207, 218 would overlap or appear adjacent or superimposed upon more than one instrument, thus causing confusion to the clinician. As shown in FIG. 6B, to remedy this issue, the badge 207 is moved a shift distance from its default location near the distal end of the joint region 234 along a longitudinal axis A1 of the instrument 26a. In this embodiment, the badge 207 is relocated to a distal end of the shaft 232 of the instrument 26a. Similarly, the badge 218 is moved a shift distance from its default location near the distal end of the joint region 244 along a longitudinal axis A2 of the instrument 26c. In this embodiment, the badge 218 is relocated to a distal end of the shaft 242 of the instrument 26c. The shift distance may correspond to the position of the badge relative to a calibrated kinematic model of the instrument as coupled to the arm and spar and/or may correspond to the size of the instrument distal end portions in the field of view 202. For example, the calibrated kinematic model (based, for example, on knowledge of the manipulator joint positions, kinematic sensors, size of components in the kinematic chain) provides the position and orientation of the joint region 234 of the instrument 26a in the surgical environment. An uncertainty factor is associated with the determined position orientation of the joint region 234 due to uncertainty in the kinematic model. Based on the kinematic model, the kinematic uncertainty factors for all of the instruments in the field of view, and the default locations for the badges, the teleoperational system may determine a proximity factor (e.g. a center-to-center or edge-to-edge distance, a percentage of overlap) indicating whether the badges overlap or are sufficiently close to each other as to create ambiguity to a clinician if the badges remain in the default locations. If the proximity factor is less than a predetermined interference distance, the badges are adjusted as needed to raise the proximity factor above the predetermined interference distance. For example, in some embodiments, the badges can be moved along or across the axis of the instruments by at least a minimum shift distance. In other embodiments, the badges can be resized or reshaped to maintain an acceptable interference distance while still providing the desired informational content. In this way, the badges 207, 218 remain clearly associated with their respective medical instruments 26a, 26c and also remain clearly readable.

Figure 7A:
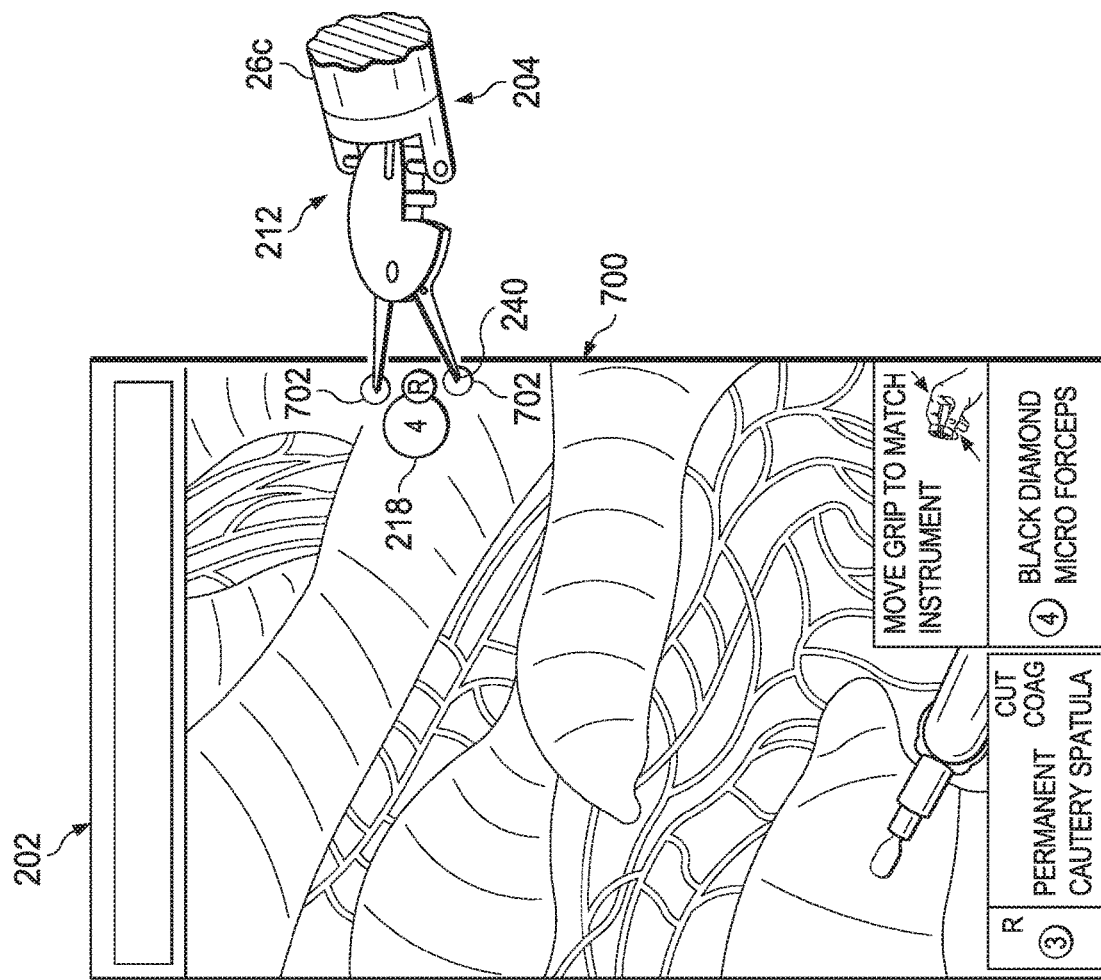
FIGS. 7A-7C illustrate the behavior of the association information badge as the associated medical instrument nears the edge of the image of the surgical environment, and as the medical instrument moves outside of the image of the surgical environment.
Figure 7B:
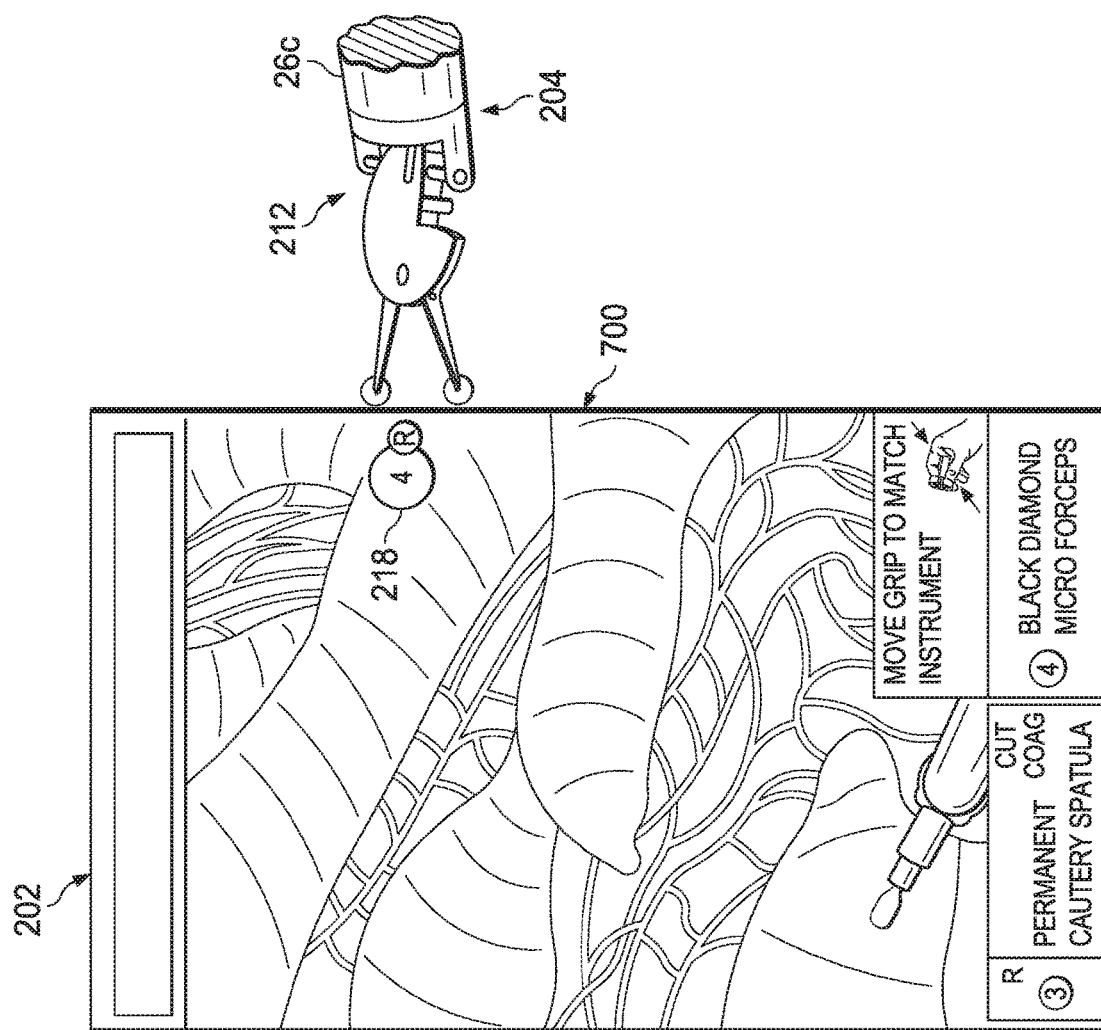
Figure 7C:
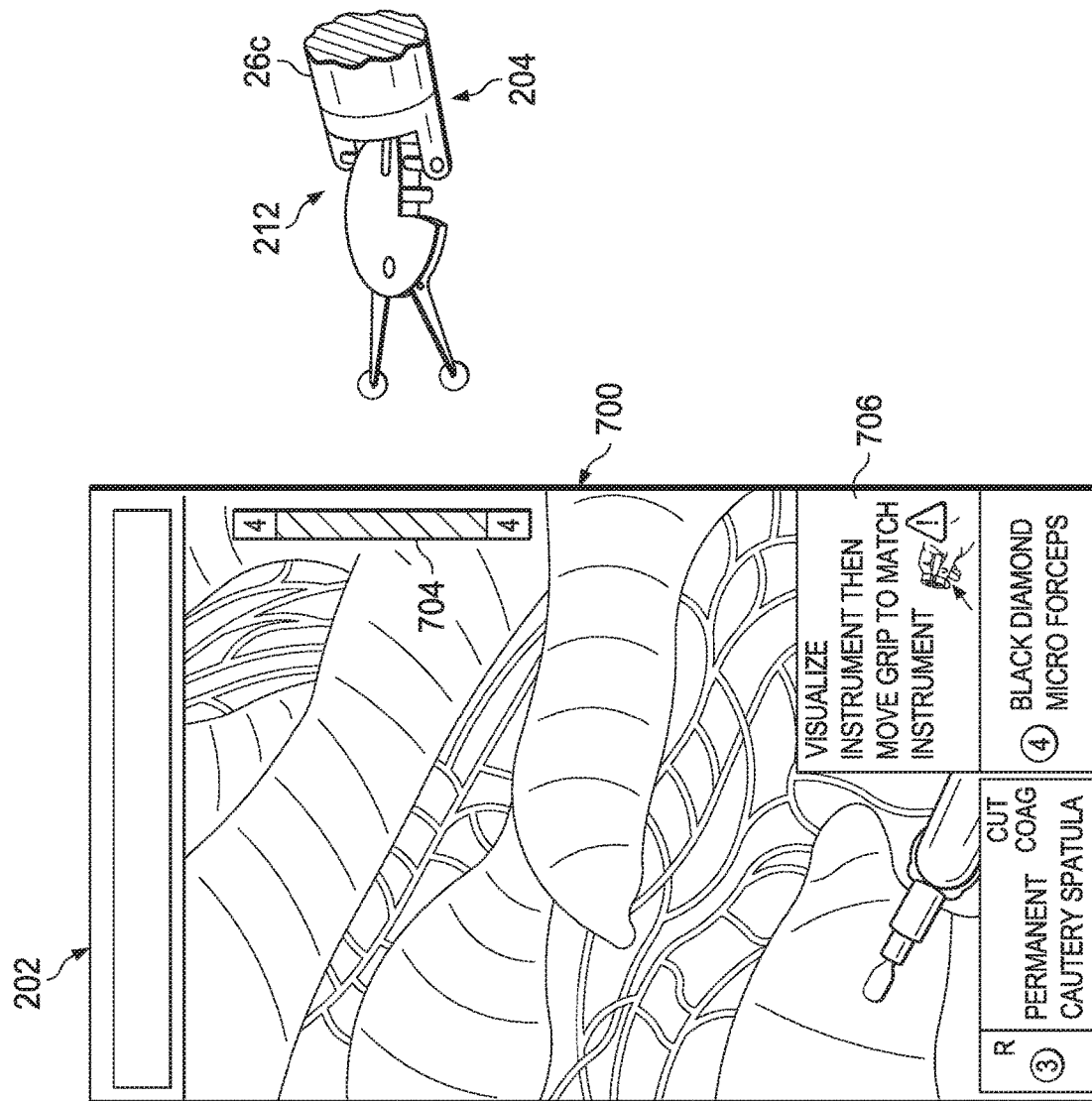

Referring now to FIGS. 7A-7C, a badge with its association information may be particularly useful when a medical instrument approaches a boundary of the image 202 of the field of view or moves out of the image 202. FIG. 7A illustrates the displayed image 202 of a field of view of the imaging instrument in the surgical environment 200. The displayed image has a boundary 700. The distal end portion of medical instrument 26c, particularly the end effector tip 240, is within the boundary 700 and is visible in the displayed image 202. The determination of whether the instrument 26c is inside or outside of the field of view of the imaging instrument may be based upon the calculated location of the end effector tips 240. Because of small error factors associated with the teleoperational system, the instrument, and/or the imaging system, the determination of the location of the tips 240 with respect to the imaging instrument has an associated cumulative error factor. To avoid providing false-positive out-of-view indicators to a clinician, the determination of whether an instrument tip is out of the imaging system field of view may be biased by estimating the range of possible locations for the distal tip and suppressing an out-of-view indicator if any or a designated percentage of the estimated possible locations for the distal tip are within the field of view. The sensitivity of the bias may be adjusted based upon the clinician's tolerance for false-positive out-of-view indicators. A set of error bounding volumes 702 is associated with the tip 240. The bounding volumes 702 may be displayed graphically in the image 202 or may be associated with the tip 240 without being displayed. The error bounding volumes may represent the predicted locations of the distal and proximal ends of the tip portions to within a high degree of certainty such as 90-99%. The error bounding volume 702 represents the predicted locations of the tip 240 of the instrument 26c. Further description of the error calculation and bounding volumes is provided in U.S. Provisional App. No. 61/954,442, filed Mar. 17, 2014, disclosing "Systems and methods for off-screen indication of instruments in a teleoperational medical system," which is incorporated by reference herein in its entirety.

As shown in FIG. 7A, the bounding volumes 702 are within the field of view bounded by the boundary 700. The bounding volumes 702 may or may not be rendered in the image 202, but their location relative to the boundary may be determined by the system regardless of whether they are displayed. Since the medical instrument 26c is visible in the display and the bounding volumes are within the boundary 700, the badge 218 is accordingly displayed on the image 202 of the field of view. In order to maintain visibility and readability, the badge 218 remains completely inside the boundary 700, even if the distal end portion of the instrument 26c, to which the badge 206 is attached, is partially outside the boundary 700, as shown here. This allows the clinician to clearly locate the medical instrument 26c even if it is only barely visible within the image 202. In FIG. 7B the medical instrument 26c is not visible in the displayed image 202. In some embodiments, the system may terminate display of the badge 218 when the associated medical instrument 26c is not visible in the image 202. Because the medical instrument 204 may be teleoperationally controlled without being visible in the field of view to a clinician, inadvertent movement of an instrument outside of the field of view creates a safety risk. Additionally, clinicians may lose track of instruments that are located outside of the field of view. To minimize these risks, out-of-view instrument indicators may be visually or audibly presented to increase the clinician's awareness of the location of instruments not visible within the field of view. However, in FIG. 7B the bounding volumes 702 for medical instrument 26c are within the boundary 700 indicating that the location of the tip 240 relative to the boundary 700 is uncertain. Therefore, while the bounding volumes 702 remain within the boundary 700, the badge 218 remains on the image 202 even if the image 202 does not appear to include the tip 240.

Once the medical instrument 204 is far enough outside the boundary 700 that the bounding volumes 702 are also outside of the boundary, an out-of-view instrument indicator 704 is provided along the boundary 700 of the image 202 of the field of view, as shown in FIG. 7C, to indicate that medical instrument 26c is located out of the field of view in the general direction of the indicator. In this embodiment, the indicator 704 is a graphical bar, but in other embodiments may be a series of dots, or an icon, an alpha-numeric indicator. In addition to or alternative to the visual indicator 704, an audible out-of-view indicator such as a beeping sound or a language-based instruction may alert the clinician that the medical instrument 204 is out of the field of view. The audible cue may pan between left and right speakers of the surgeon's console to reinforce the instrument position relative to the view. Alternatively, the audible cue may emit from the left or right speaker in correspondence with the left or right hand control associated with the instrument. In addition to or alternative to the visual indicator 704, textual information 706 related to the out-of view instrument may be provided to alert the clinician and/or to provide identifying information about the instrument or an instruction to visualize the instrument. In various embodiments, the out-of-view indicator 704 is mutually exclusive with the badge 218. When the badge 218 is displayed the out-of-view indicator 704 is not displayed, and vice versa. This provides the clinician with constant knowledge of the location of the medical instrument 26c.

In various embodiments, the use of an out-of-view indicator may be limited to avoid becoming a distraction to the clinician. The use of the out-of-view indicator may be context-sensitive such that the out-of-view indicator may only be displayed during certain states of operation of the teleoperational system. For example, the out-of-view indicator may be displayed during a state of the system in which the operator controls movement of the imaging system, a state which may be known as a camera control state. As another example, the out-of-view indicator may be displayed while the system awaits input from the operator to take control of an associated instrument, described above as the disengaged state. As another example, the out-of-view indicator may be displayed for a few seconds after initiating a state of the system in which the operator controls movement of the instruments, described above as the engaged state. In still other alternative embodiments, the out-of-view indicator may be disabled or selectively enabled when the clinician wants to learn about the location of out-of-view instruments. In some embodiments, the clinician must provide an acknowledgement that the instrument tip is outside of the field of view before operation of the out of view instrument is enabled. Additional warnings or acknowledgements may be used for energy emitting devices, sharp devices, or devices that provide an increased patient risk if used without visualization. Further description of an out-of-view indicator system is provided in U.S. Provisional App. No. 61/954,442 which is incorporated by reference above.

Figure 8:
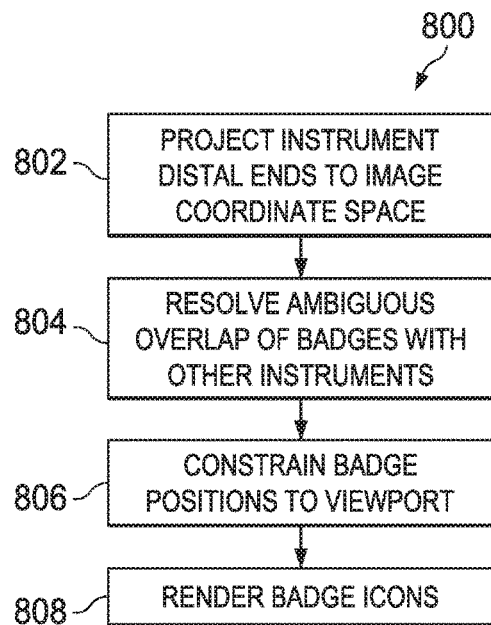
FIG. 8 illustrates a method of rendering badges within an image of the field of view of the surgical workspace.
Figure 9:
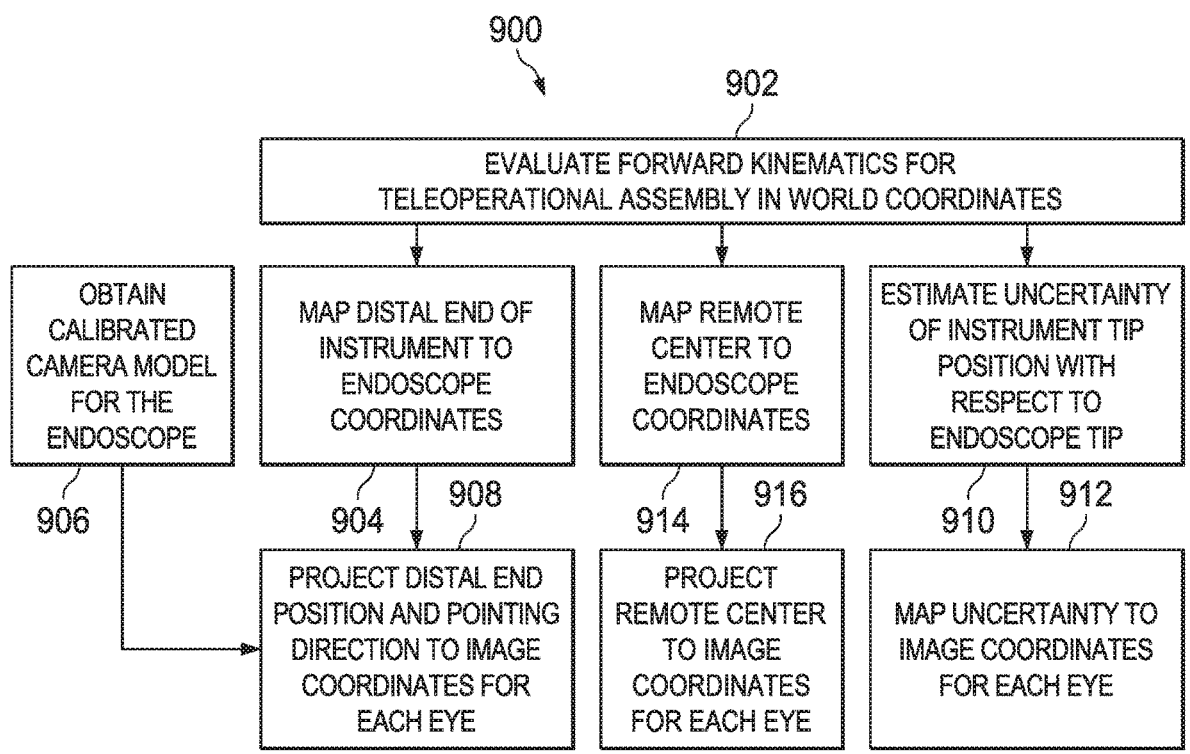
FIG. 9 illustrates in detail the process of FIG. 8 wherein the locations of medical instrument distal end portions are projected into a coordinate space of the image of the field of view of the surgical workspace.

As explained above, the badges may be positioned and sized to correspond with the images of the instrument distal ends with which they are associated. FIGS. 8-11 provide further detail for preserving this physical correspondence. FIG. 8 illustrates a method 800 of rendering badges within image 202. At process 802 the locations of medical instrument distal end portions are projected into a coordinate space of the image 202. FIG. 9 illustrates a method 900 for performing the process 802. At process 902, the forward kinematics of the teleoperational assembly are evaluated to determine the position and orientation of the medical instruments (including the imaging device) within a world coordinate system (e.g., a surgical environment coordinate space $F_W$). More specifically, the kinematics associated with the respective set of links and teleoperational manipulator for each medical instrument is determined in the world coordinate system. The world coordinate system is a set of Cartesian coordinates that is established with reference to the surgical environment within which the teleoperational system is located.

At process 904 the position and orientation of the distal end portion of each medical instrument (e.g. in the instrument coordinate space $F_I$) is mapped to an endoscope coordinate system (e.g. imaging device coordinate space $F_E$). The endoscope coordinate system is a set of Cartesian coordinates that is established with its origin at the distal tip of the endoscope. By using the forward kinematics of the endoscope and the forward kinematics of each medical instrument in the world coordinate system, as determined at process 902, the medical instrument distal end position and orientation relative to the endoscope tip position and orientation may be computed in the endoscope coordinate system. Generally, the default location for the badges may be at or near a kinematic endpoint of the medical instrument.

At process 906 a calibrated camera model is obtained for the endoscope. The calibrated camera model is a mapping from endoscope coordinate space to the right and left eye image coordinate spaces. In one embodiment, the mapping is accomplished with a series of three transforms. First, a modelview transform maps from the endoscope coordinate space (at the distal tip of the endoscope) into an eye coordinate space for the endoscope, accounting for interocular separation of the stereoscopic cameras in the imaging system and for differences in coordinate system conventions. Second, a perspective projection transform maps from the eye coordinate space to normalized coordinates (e.g., −1, +1) and accounts for perspective of the endoscope field of view and convergence distance. Third, a viewport bounds transform maps from the normalized eye coordinates to the right and left eye image coordinate spaces. In one embodiment, these three transforms can be combined into one 4×4 homogenous transform for each of the right and left eye images.

At process 908 the calibrated camera model is used to project points and vectors from endoscope coordinate space to the image coordinate space for each eye. More specifically the calibrated camera model projects the medical instrument distal end position and orientation to a right eye image coordinate space and a left eye image coordinate space to provide a stereoscopic 3D image to the clinician.

At process 910, uncertainties in the kinematic model of the teleoperational system, which result in corresponding uncertainties in the position of the distal end portion of the associated medical instrument, are estimated with respect to the endoscope tip. At process 912 these uncertainties are mapped to the right and left eye image coordinate spaces from which the clinician views the three dimensional image 202.

At process 914, using the forward kinematics determined at process 902, the kinematic remote center (e.g., the incision site about which the instruments pivot) is mapped to the endoscope coordinate space. At process 916, the calibrated camera model is used to project the remote center to the image coordinate systems for each eye in a similar manner as described in process 908.

The processes 902-916 may be repeated for each medical instrument in the teleoperational system so that all medical instruments are properly projected into the stereoscopic 3D image 202. The processes may be performed in sequence or in parallel, and one or more process may be updated while the others are not.

Figure 10:
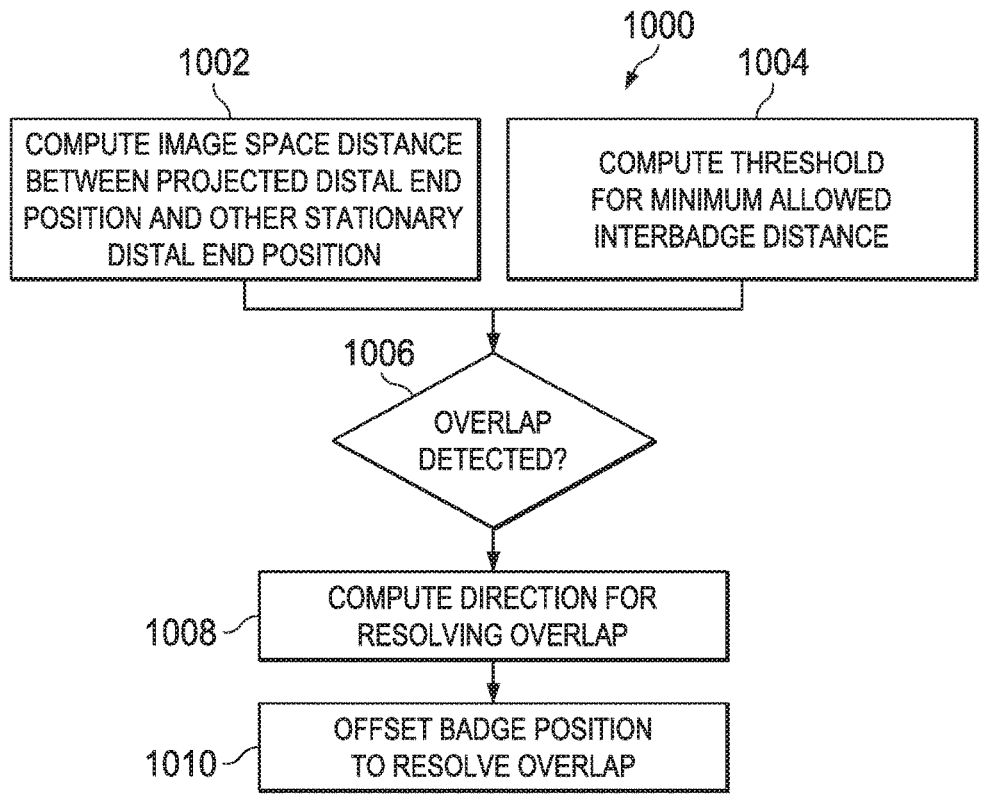
FIG. 10 illustrates in detail the process of FIG. 8 wherein potential overlap of badges is checked for and resolved. In this case there are at least two medical instruments.

Referring again to FIG. 8, the rendering of badge graphics is based upon a consideration of multiple display factors including, for example, the default locations at or near the distal tip of the distal ends of the medical instruments, the potential ambiguity associated with overlapping or indeterminate badge placement, the constraints imposed by the endoscope viewport, and the system rules for hidden instruments. The position of the badge graphics may be determined in image coordinate space for each eye. At a process 804, potential overlap of badges is checked for and resolved to reduce the likelihood that a badge is spatially associated with the wrong instrument. FIG. 10 illustrates a method 1000 for performing the process 804 of FIG. 8. In this embodiment, at least two medical instruments are positioned in the surgical space. As described above, the default location for rendering the badge is at the distal end portion of a medical instrument. At process 1002, the distance in image space coordinates between the distal end portions of two medical instruments is calculated. At process 1004, a threshold for minimum allowed inter-badge distance is calculated. The threshold for minimum allowed inter-badge distance is the maximum of the sum of the projected radii (or, if the badge is not circular, another maximum dimension from the center of the badge) of the badges plus the maximum of the sum of the projected uncertainty of badge positions. At process 1006, the image space distance between the two distal end portions is compared to the calculated threshold distance to determine whether their associated badges overlap or may be perceived to overlap. If overlap is detected, at process 1008 a direction to move the badge to resolve the overlap is computed. The direction to move the badge is determined by the unit vector between the instrument distal end portion and the remote center projected into image coordinate space (as determined in processes 908 and 916). Further if overlap is detected, at process 1010 a distance to translate the badge to resolve overlap is determined. The distance that the badges are offset is computed as the difference between the minimum allowed inter-badge distance and the current distance between the distal end portions. The offset prevents badge graphics from overlapping and provides badge positions that are sufficiently spaced to avoid uncertainty in instrument association.

Figure 11:
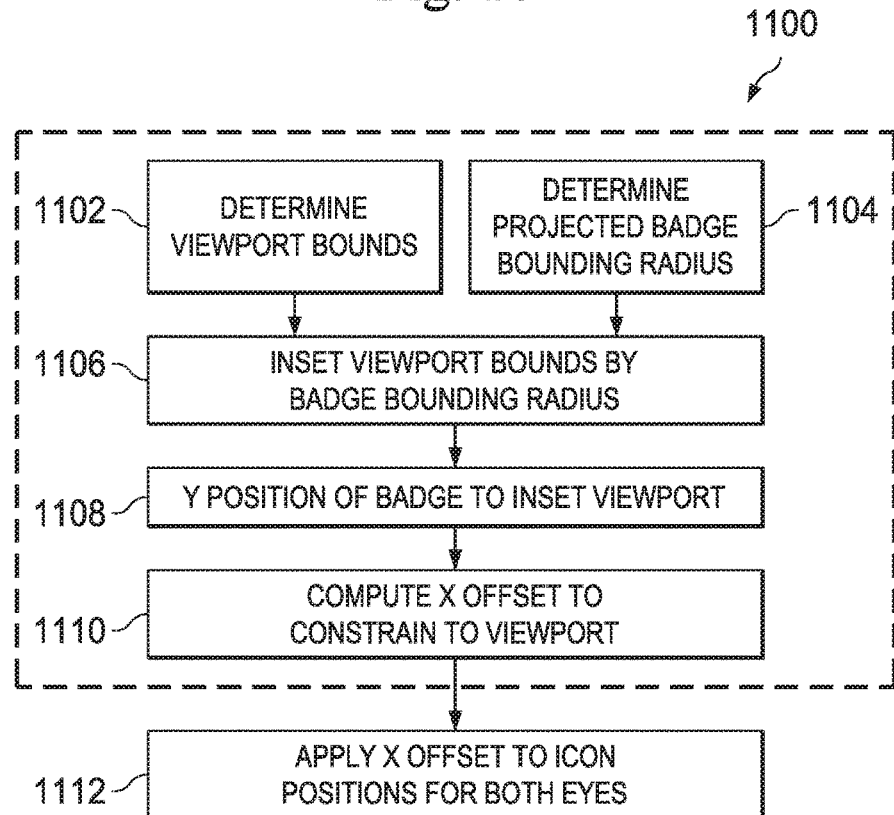
FIG. 11 illustrates in detail the process of FIG. 8 wherein badges are constrained to the viewable space of the image of the field of view of the surgical workspace.

Referring again to FIG. 8, at a process 806 badges are constrained to the viewable space of image 202, which corresponds to the boundaries of the endoscope viewport at the distal tip of the endoscope. This process may place the badge graphics within the boundaries of the image 202 without clipping any of the graphics. This process may also control the perceived depth of the badge by preventing modification to the horizontal disparity if the badges are shifted to avoid the image boundaries or to prevent ambiguity. FIG. 11 illustrates a method 1100 for performing the process 806 of FIG. 8. At process 1102, the right eye boundary of the viewable space of image 202, corresponding to the endoscope viewport, is determined. At process 1104 the projected radius of the badge graphic is determined for the right eye. At process 1106, for the right eye, the boundary is inset by the projected badge radius to create an inset boundary. At process 1108 the Y position of the center of the badge is adjusted to remain within the inset boundary for the right eye. At process 1110 the offset of the X position of the center of the badge which is necessary to keep the badge completely within the inset boundary is computed. Processes 1102 through 1110 are repeated for the left eye images. To maintain the proper apparent depth in stereoscopic 3D, the badge must be adjusted the same amount in both the right and left eye images. This maintains the horizontal disparity required for the proper perceived depth of the badge. At process 1112, the X offset which was computed at process 1110 for one of the right or left eye images is applied to the X position of the badge in both the right and left eye images. In some embodiments, the larger X offset value is chosen to prevent the possibility that the badge graphic will be even partially outside of the boundary 700.

Referring again to FIG. 8, at process 808, the badges are rendered within the left and right eye displays to form the image 202 based on the calculations made in processes 802, 804 and 806.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
    a teleoperational assembly including an operator control system and a plurality of manipulators configured for teleoperation by the operator control system, wherein a first manipulator of the plurality of manipulators is configured to control movement of a first medical instrument in a surgical environment, a second manipulator of the plurality of manipulators is configured to control movement of a second medical instrument in the surgical environment, and a third manipulator of the plurality of manipulators is configured to control movement of an imaging instrument; and
    a processing unit including one or more processors, wherein the processing unit is configured to:
        determine an initial position for a first badge associated with a distal end portion of the first medical instrument;
        determine an initial position for a second badge associated with a distal end portion of the second medical instrument;
        evaluate a display factor based on the initial positions of the first and second badges;
        determine a display position for the first badge in an image coordinate space based on the display factor; and
        determine a display position for the second badge in the image coordinate space based on the display factor.

2. The system of claim 1 wherein evaluating a display factor includes determining whether the initial position for the first badge overlaps the initial position for the second badge.

3. The system of claim 1 wherein evaluating a display factor includes determining whether the initial position for the first badge overlaps the distal end portion of the second medical instrument in an image of the surgical environment.

4. The system of claim 1 wherein evaluating a display factor includes:
    determining a distance between the distal end portions of the first and second medical instruments in an image of the surgical environment;
    comparing the distance to a predetermined inter-badge distance threshold;
    determine a direction component by which to modify the initial position of the first badge to generate the display position for the first badge; and
    determine a translation component by which to modify the initial position of the first badge to generate the display position for the first badge.

5. The system of claim 1 wherein evaluating a display factor includes evaluating whether the initial positions for the first and second badges are within a boundary of an image of the surgical environment.

6. The system of claim 1 wherein evaluating a display factor includes:
    defining an inset boundary for an image of the surgical environment based on bounding radii of the first and second badges; and
    generating the display position for the first badge by adjusting a Y position value of the initial position of the first badge to constrain the first badge within the inset boundary.

7. The system of claim 1 wherein the display position for the first badge includes right eye and left eye display positions and wherein evaluating a display factor includes:
    defining an inset boundary for an image of the surgical environment based on bounding radii of the first and second badges; and
    generating the display position for the first badge by computing an X position offset for the initial position of the first badge to constrain the first badge within the inset boundary and by applying the X position offset to generate the right eye and left eye display positions.

8. The system of claim 1 wherein the processing unit is further configured to:
    evaluate a forward kinematic model for the first manipulator to determine a position of the distal end portion of the first medical instrument;
    evaluate a forward kinematic model for the second manipulator to determine a position of the distal end portion of the second medical instrument;
    mapping the positions of the distal end portions of the first and second medical instruments to an imaging instrument tip coordinate space;
    obtaining a calibrated camera transform for the imaging instrument; and
    projecting the positions of the distal end portions of the first and second medical instruments to a right eye image coordinate space and to a left eye image coordinate space.

9. The system of claim 8 wherein the processing unit is further configured to:
    evaluate a forward kinematic model for the third manipulator to determine a position of an imaging instrument distal tip.

10. The system of claim 8 wherein the calibrated camera transform consists of a model view transform, a perspective projection transform, and a viewport bounds transform.

11. A method comprising:
   displaying an image of a surgical environment, the image obtained by an imaging instrument and including an image of a distal end of a first medical instrument and an image of a distal end of a second medical instrument, wherein the first medical instrument is coupled to a first manipulator of a teleoperational assembly and the second medical instrument is coupled to a second manipulator of the teleoperational assembly;
   determining an initial position for a first badge associated with the distal end of the first medical instrument;
   determining an initial position for a second badge associated with the distal end of the second medical instrument;
   evaluating a display factor based on the initial positions of the first and second badges determining a display position for the first badge in an image coordinate space based on the display factor; and
   determining a display position for the second badge in the image coordinate space based on the display factor.

12. The method of claim 11 wherein evaluating a display factor includes determining whether the initial position for the first badge overlaps the initial position for the second badge.

13. The method of claim 11 wherein evaluating a display factor includes determining whether the initial position for the first badge overlaps the distal end of the second medical instrument in the image of the distal end of the second medical instrument.

14. The method of claim 11 wherein evaluating a display factor includes:
   determining a distance between the distal ends of the first and second medical instruments in the image of the surgical environment;
   comparing the distance to a predetermined inter-badge distance threshold;
   determining a direction component by which to modify the initial position of the first badge to generate the display position for the first badge; and
   determining a translation component by which to modify the initial position of the first badge to generate the display position for the first badge.

15. The method of claim 11 wherein evaluating a display factor includes evaluating whether the initial positions for the first and second badges are within a boundary of the image of the surgical environment.

16. The method of claim 11 wherein evaluating a display factor includes:
   defining an inset boundary for the image of the surgical environment based on bounding radii of the first and second badges; and
   generating the display position for the first badge by adjusting a Y position value of the initial position of the first badge to constrain the first badge within the inset boundary.

17. The method of claim 11 wherein the display position for the first badge includes right eye and left eye display positions and wherein evaluating a display factor includes:
   defining an inset boundary for the image of the surgical environment based on bounding radii of the first and second badges; and
   generating the display position for the first badge by computing an X position offset for the initial position of the first badge to constrain the first badge within the inset boundary and by applying the X position offset to generate the right eye and left eye display positions.

18. The method of claim 11 further comprising:
   evaluating a forward kinematic model for the first manipulator to determine a position of the distal end of the first medical instrument;
   evaluating a forward kinematic model for the second manipulator to determine a position of the distal end of the second medical instrument;
   mapping the positions of the distal ends of the first and second medical instruments to an imaging instrument tip coordinate space;
   obtaining a calibrated camera transform for the imaging instrument; and
   projecting the positions of the distal ends of the first and second medical instruments to a right eye image coordinate space and to a left eye image coordinate space.

19. The method of claim 18 further comprising:
   evaluating a forward kinematic model for a third manipulator, to which the imaging instrument is coupled, to determine a position of an imaging instrument distal tip.

20. The method of claim 18 wherein the calibrated camera transform consists of a model view transform, a perspective projection transform, and a viewport bounds transform.

* * * * *